United States Patent
Bates et al.

(10) Patent No.: US 7,611,533 B2
(45) Date of Patent: *Nov. 3, 2009

(54) COATED IMPLANTABLE MEDICAL DEVICE

(75) Inventors: Brian L. Bates, Bloomington, IN (US); Anthony O. Ragheb, West Layfayette, IN (US); Neal E. Fearnot, West Lafayette, IN (US); Thomas G. Kozma, Alpharetta, GA (US); William D. Voorhees, III, West Lafayette, IN (US); Thomas A. Osborne, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/223,415

(22) Filed: Aug. 19, 2002

(65) Prior Publication Data

US 2003/0036794 A1    Feb. 20, 2003

Related U.S. Application Data

(63) Continuation-in-part of application No. 09/027,054, filed on Feb. 20, 1998, now Pat. No. 6,774,278, and a continuation-in-part of application No. 08/645,646, filed on May 16, 1996, now Pat. No. 6,096,070, which is a continuation-in-part of application No. 08/484,532, filed on Jun. 7, 1995, now Pat. No. 5,609,629.

(60) Provisional application No. 60/038,459, filed on Feb. 20, 1997.

(51) Int. Cl.
*A61F 2/06* (2006.01)
(52) U.S. Cl. ..................... 623/1.42; 623/1.43
(58) Field of Classification Search ....... 623/1.42–1.46; 604/264, 265, 891.1, 892.1
See application file for complete search history.

(56) References Cited

U.S. PATENT DOCUMENTS 4,101,984 A    7/1978    MacGregor (Continued)

FOREIGN PATENT DOCUMENTS

EP    0747069 A2 *    12/1996

OTHER PUBLICATIONS

Final Office Action dated Apr. 21, 2006, U.S. Appl. No. 10/218,308.
Final Office Action dated Apr. 25, 2007, U.S. Appl. No. 10/414,444.
Final Office Action dated Aug. 15, 2007, U.S. Appl. No. 10/218,305.
Final Office Action dated Dec. 7, 2005, U.S. Appl. No. 10/414,444.
Final Office Action dated Jan. 11, 2008, U.S. Appl. No. 10/218,308.

(Continued)

*Primary Examiner*—Paul Prebilic
(74) *Attorney, Agent, or Firm*—Woodard, Emhardt, Moriarty, McNett & Henry LLP

(57) ABSTRACT

A coated implantable medical device 10 includes a structure 12 adapted for introduction into the vascular system, esophagus, trachea, colon, biliary tract, or urinary tract, and at least one layer 18 of an immunosuppressive agent posited over at least one surface of the structure 12. Optionally, the device 10 can include at least one porous, preferably polymeric layer 20 posited over the layer 18 of immunosuppressive agent, and can alternatively or additionally include at least one coating layer 16 posited on one surface of the structure 12, the at least one layer 18 of immunosuppressive agent being posited in turn on at least a portion of the coating layer 16. The porous layer 20 and the coating layer 16 each provide for the controlled release of the bioactive material from the device 10. The structure 12 is preferably configured as a coronary stent. The polymer of the porous layer 20 is preferably applied by vapor or plasma deposition. It is particularly preferred that the polymer is a polyamide, parylene or a parylene derivative which is deposited without solvents, heat or catalysts, but rather by condensation of a monomer vapor.

12 Claims, 5 Drawing Sheets

U.S. PATENT DOCUMENTS

| | | | |
|---|---|---|---|
| 4,305,926 A | 12/1981 | Everse et al. | |
| 4,343,788 A | 8/1982 | Mustacich et al. | |
| 4,365,359 A | 12/1982 | Raab | |
| 4,476,590 A | 10/1984 | Scales et al. | |
| 4,479,795 A | 10/1984 | Mustacich et al. | |
| 4,502,159 A | 3/1985 | Woodroof et al. | |
| 4,677,143 A | 6/1987 | Laurin et al. | |
| 4,769,013 A | 9/1988 | Lorenz et al. | |
| 4,793,825 A | 12/1988 | Benjamin et al. | |
| 4,872,867 A | 10/1989 | Joh | |
| 4,879,135 A | 11/1989 | Greco et al. | |
| 4,886,062 A | 12/1989 | Wiktor | |
| 4,909,799 A | 3/1990 | Thulesius et al. | |
| 4,917,686 A | 4/1990 | Bayston et al. | |
| 4,925,668 A | 5/1990 | Khan et al. | |
| 4,950,256 A | 8/1990 | Luther et al. | |
| 4,994,047 A | 2/1991 | Walker et al. | |
| 5,004,461 A | 4/1991 | Wilson | |
| 5,019,096 A | 5/1991 | Fox, Jr. et al. | |
| 5,019,393 A | 5/1991 | Ito et al. | |
| 5,019,601 A | 5/1991 | Allen | |
| 5,053,048 A | 10/1991 | Pinchuk | |
| 5,059,166 A | 10/1991 | Fischell et al. | |
| 5,067,491 A | 11/1991 | Taylor, II et al. | |
| 5,092,841 A * | 3/1992 | Spears | 604/103.01 |
| 5,098,977 A | 3/1992 | Frautschi et al. | |
| 5,102,402 A | 4/1992 | Dror et al. | |
| 5,108,424 A | 4/1992 | Hoffman, Jr. et al. | |
| 5,112,457 A | 5/1992 | Marchant | |
| 5,135,516 A | 8/1992 | Sahatjian et al. | |
| 5,163,952 A | 11/1992 | Froix | |
| 5,165,952 A | 11/1992 | Solomon et al. | |
| 5,171,217 A | 12/1992 | March et al. | |
| 5,182,317 A | 1/1993 | Winters et al. | |
| 5,197,977 A | 3/1993 | Hoffman, Jr. et al. | |
| 5,217,493 A | 6/1993 | Raad et al. | |
| 5,222,971 A | 6/1993 | Willard et al. | |
| 5,229,172 A | 7/1993 | Cahalan et al. | |
| 5,236,447 A * | 8/1993 | Kubo et al. | 623/1.13 |
| 5,244,654 A | 9/1993 | Narayanan | |
| 5,282,823 A | 2/1994 | Schwartz et al. | |
| 5,282,850 A | 2/1994 | Davidson | |
| 5,288,711 A * | 2/1994 | Mitchell et al. | 514/56 |
| 5,298,255 A | 3/1994 | Sawamoto et al. | |
| 5,304,121 A | 4/1994 | Sahatjian | |
| 5,314,688 A | 5/1994 | Kauffman et al. | |
| 5,342,348 A | 8/1994 | Kaplan | |
| 5,344,411 A | 9/1994 | Domb et al. | |
| 5,344,444 A | 9/1994 | Glastra | |
| 5,345,933 A | 9/1994 | Peterson et al. | |
| 5,348,873 A | 9/1994 | Matsuda et al. | |
| 5,356,433 A | 10/1994 | Rowland et al. | |
| 5,380,299 A * | 1/1995 | Fearnot et al. | 604/265 |
| 5,383,927 A | 1/1995 | De Goicoechea et al. | |
| 5,383,928 A | 1/1995 | Scott et al. | |
| 5,419,760 A | 5/1995 | Narciso, Jr. | |
| 5,443,458 A | 8/1995 | Eury | |
| 5,447,724 A * | 9/1995 | Helmus et al. | 424/426 |
| 5,449,382 A | 9/1995 | Dayton | |
| 5,454,886 A | 10/1995 | Burrell et al. | |
| 5,455,040 A | 10/1995 | Marchant | |
| 5,456,663 A | 10/1995 | Lemelson | |
| 5,457,113 A | 10/1995 | Cullinan et al. | |
| 5,464,450 A | 11/1995 | Buscemi et al. | |
| 5,464,650 A | 11/1995 | Berg et al. | |
| 5,500,013 A * | 3/1996 | Buscemi et al. | 623/1.22 |
| 5,510,330 A | 4/1996 | Martin et al. | |
| 5,531,716 A | 7/1996 | Luzio et al. | |
| 5,534,288 A | 7/1996 | Gruskin et al. | |
| 5,554,181 A | 9/1996 | Das | |
| 5,567,495 A | 10/1996 | Modak et al. | |
| 5,569,463 A | 10/1996 | Helmus et al. | |
| 5,578,075 A * | 11/1996 | Dayton | 623/1.15 |
| 5,605,696 A | 2/1997 | Eury et al. | |
| 5,607,463 A | 3/1997 | Schwartz et al. | |
| 5,607,475 A | 3/1997 | Cahalan et al. | |
| 5,609,629 A * | 3/1997 | Fearnot et al. | 623/1.42 |
| 5,624,411 A | 4/1997 | Tuch | |
| 5,629,008 A * | 5/1997 | Lee | 424/426 |
| 5,649,977 A * | 7/1997 | Campbell | 623/1.15 |
| 5,679,400 A | 10/1997 | Tuch | |
| 5,681,846 A | 10/1997 | Trissel | |
| 5,697,967 A | 12/1997 | Dinh et al. | |
| 5,716,981 A | 2/1998 | Hunter et al. | |
| 5,733,327 A | 3/1998 | Igaki et al. | |
| 5,762,638 A | 6/1998 | Shikani et al. | |
| 5,770,198 A | 6/1998 | Coller et al. | |
| 5,772,640 A | 6/1998 | Modak et al. | |
| 5,820,607 A | 10/1998 | Tcholakian et al. | |
| 5,824,049 A * | 10/1998 | Ragheb et al. | 623/1.44 |
| 5,837,008 A | 11/1998 | Berg et al. | |
| 5,853,745 A | 12/1998 | Darouiche | |
| 5,873,904 A | 2/1999 | Ragheb et al. | |
| 5,886,026 A | 3/1999 | Hunter et al. | |
| 5,902,283 A | 5/1999 | Darouiche et al. | |
| 6,096,070 A * | 8/2000 | Ragheb et al. | 623/1.39 |
| 6,171,232 B1 | 1/2001 | Papandreou et al. | |
| 6,240,616 B1 | 6/2001 | Yan | |
| 6,273,908 B1 | 8/2001 | Ndondo-Lay | |
| 6,273,913 B1 * | 8/2001 | Wright et al. | 623/1.42 |
| 6,299,604 B1 * | 10/2001 | Ragheb et al. | 604/265 |
| 6,306,166 B1 | 10/2001 | Barry et al. | |
| 6,335,029 B1 | 1/2002 | Kamath et al. | |
| 6,379,382 B1 * | 4/2002 | Yang | 623/1.42 |
| 6,387,379 B1 | 5/2002 | Goldbert et al. | |
| 6,599,275 B1 | 7/2003 | Fischer et al. | |
| 6,730,064 B2 * | 5/2004 | Ragheb et al. | 604/265 |
| 6,774,278 B1 | 8/2004 | Ragheb et al. | |
| 6,918,927 B2 | 7/2005 | Bates et al. | |
| 7,208,010 B2 * | 4/2007 | Shanley et al. | 623/1.42 |
| 7,326,245 B2 | 2/2008 | Rosenthal et al. | |
| 2002/0007209 A1* | 1/2002 | Scheerder et al. | 623/1.15 |
| 2002/0013616 A1* | 1/2002 | Carter et al. | 623/1.15 |
| 2002/0111590 A1* | 8/2002 | Davila et al. | 604/265 |
| 2003/0028243 A1 | 2/2003 | Bates et al. | |
| 2003/0028244 A1 | 2/2003 | Bates et al. | |
| 2003/0036794 A1 | 2/2003 | Ragheb et al. | |
| 2004/0047909 A1 | 3/2004 | Ragheb et al. | |
| 2004/0068241 A1 | 4/2004 | Fischer et al. | |
| 2004/0073284 A1 | 4/2004 | Bates et al. | |
| 2004/0243225 A1 | 12/2004 | Ragheb et al. | |
| 2005/0042295 A1 | 2/2005 | Hunter et al. | |
| 2005/0123605 A1 | 6/2005 | Hunter et al. | |
| 2007/0020382 A1* | 1/2007 | Hossainy et al. | 427/2.25 |
| 2007/0026131 A1* | 2/2007 | Hossainy et al. | 427/2.21 |

OTHER PUBLICATIONS

Final Office Action dated Jun. 6, 2007, U.S. Appl. No. 10/414,444.
Final Office Action dated Mar. 14, 2005, U.S. Appl. No. 10/218,308.
Final Office Action dated Mar. 22, 2006, U.S. Appl. No. 10/218,305.
Final Office Action dated May 11, 2006, U.S. Appl. No. 10/870,079.
Final Office Action dated May 16, 2005, U.S. Appl. No. 10/218,305.
Non-final Office Action dated Dec. 1, 2004, U.S. Appl. No. 10/218,305.
Non-final Office Action dated Dec. 2, 2005, U.S. Appl. No. 10/870,079.
Non-final Office Action dated Feb. 12, 2007, U.S. Appl. No. 10/218,305.
Non-final Office Action dated Feb. 12, 2007, U.S. Appl. No. 10/218,308.
Non-final Office Action dated Feb. 8, 2007, U.S. Appl. No. 10/870,079.

Non-final Office Action dated Jan. 10, 2008, U.S. Appl. No. 10/218,305.
Non-final Office Action dated Jul. 18, 2007, U.S. Appl. No. 10/218,308.
Non-final Office Action dated Jul. 19, 2004, U.S. Appl. No. 10/218,308.
Non-final Office Action dated Jun. 6, 2006, U.S. Appl. No. 10/414,444.
Non-final Office Action dated May 19, 2005, U.S. Appl. No. 10/414,444.
Non-final Office Action dated Oct. 6, 2005, U.S. Appl. No. 10/218,305.
Non-final Office Action dated Oct. 6, 2005, U.S. Appl. No. 10/218,308.
Non-final Office Action dated Oct. 9, 2007, U.S. Appl. No. 10/870,079.
Notice of Allowance dated Mar. 21, 2008, U.S. Appl. No. 10/414,444.
Restriction Requirement Office Action dated Jan. 12, 2005, U.S. Appl. No. 10/414,444.
Restriction Requirement Office Action dated Mar. 16, 2004, U.S. Appl. No. 10/218,305.
Restriction Requirement Office Action dated Mar. 16, 2004, U.S. Appl. No. 10/218,308.

* cited by examiner

COATED IMPLANTABLE MEDICAL DEVICE

CROSS-REFERENCE TO RELATED APPLICATIONS

This application is a continuation-in-part of non-provisional application Ser. No. 09/027,054, filed Feb. 20, 1998, now U.S. Pat. No. 6,774,278, issued Aug. 10, 2004, which claimed priority to provisional application Ser. No. 60/038,459, filed Feb. 20, 1997, now abandoned, and which was also a continuation-in-part application of and claimed priority to application Ser. No. 08/645,646, filed May 16, 1996, now U.S. Pat. No. 6,096,070, issued Aug. 1, 2000, which was in turn a continuation-in-part application of and claimed priority to application Ser. No. 08/484,532, filed Jun. 7, 1995, now U.S. Pat. No. 5,609,629, issued Mar. 11, 1997.

TECHNICAL FIELD

This invention relates generally to human and veterinary medical devices, and more particularly to devices incorporating drugs or bioactive agents.

BACKGROUND OF THE INVENTION

It has become common to treat a variety of medical conditions by introducing an implantable medical device partly or completely into the esophagus, trachea, colon, biliary tract, urinary tract, vascular system or other location within a human or veterinary patient. For example, many treatments of the vascular system entail the introduction of a device such as a stent, a catheter, a balloon, a wire guide, a cannula, or the like. However, when such a device is introduced into and manipulated through the vascular system, the blood vessel walls can be disturbed or injured. Clot formation or thrombosis often results at the injured site, causing stenosis or occlusion of the blood vessel. Moreover, if the medical device is left within the patient for an extended period of time, thrombus often forms on the device itself, again causing stenosis or occlusion. As a result, the patient is placed at risk of a variety of complications, including heart attack, pulmonary embolism, and stroke. Thus, the use of such a medical device can entail the risk of precisely the problems that its use was intended to ameliorate.

Another way in which blood vessels undergo stenosis is through disease. Probably the most common disease causing stenosis of blood vessels is atherosclerosis. Atherosclerosis is a condition which commonly affects the coronary arteries, the aorta, the iliofemoral arteries and the carotid arteries. Atherosclerotic plaques of lipids, fibroblasts, and fibrin proliferate and cause obstruction of an artery or arteries. As the obstruction increases, a critical level of stenosis is reached, to the point where the flow of blood past the obstruction is insufficient to meet the metabolic needs of the tissue distal to (downstream of) the obstruction. The result is ischemia.

Many medical devices and therapeutic methods are known for the treatment of atherosclerotic disease. One particularly useful therapy for certain atherosclerotic lesions is percutaneous transluminal angioplasty (PTA). During PTA, a balloon-tipped catheter is inserted in a patient's artery, the balloon being deflated. The tip of the catheter is advanced to the site of the atherosclerotic plaque to be dilated. The balloon is placed within or across the stenotic segment of the artery, and then inflated. Inflation of the balloon "cracks" the atherosclerotic plaque and expands the vessel, thereby relieving the stenosis, at least in part.

While PTA presently enjoys wide use, it suffers from two major problems. First, the blood vessel may suffer acute occlusion immediately after or within the initial hours after the dilation procedure. Such occlusion is referred to as "abrupt closure." Abrupt closure occurs in perhaps five percent or so of the cases in which PTA is employed, and can result in myocardial infarction and death if blood flow is not restored promptly. The primary mechanisms of abrupt closures are believed to be elastic recoil, arterial dissection and/or thrombosis. It has been postulated that the delivery of an appropriate agent (such as an antithrombic) directly into the arterial wall at the time of angioplasty could reduce the incidence of thrombotic acute closure, but the results of attempts to do so have been mixed.

A second major problem encountered in PTA is the re-narrowing of an artery after an initially successful angioplasty. This re-narrowing is referred to as "restenosis" and typically occurs within the first six months after angioplasty. Restenosis is believed to arise through the proliferation and migration of cellular components from the arterial wall, as well as through geometric changes in the arterial wall referred to as "remodeling." It has similarly been postulated that the delivery of appropriate agents directly into the arterial wall could interrupt the cellular and/or remodeling events leading to restenosis. However, like the attempts to prevent thrombotic acute closure, the results of attempts to prevent restenosis in this manner have been mixed.

Non-atherosclerotic vascular stenosis may also be treated by PTA. For example, Takayasu arteritis or neurofibromatosis may cause stenosis by fibrotic thickening of the arterial wall. Restenosis of these lesions occurs at a high rate following angioplasty, however, due to the fibrotic nature of the diseases. Medical therapies to treat or obviate them have been similarly disappointing.

A device such as an intravascular stent can be a useful adjunct to PTA, particularly in the case of either acute or threatened closure after angioplasty. The stent is placed in the dilated segment of the artery to mechanically prevent abrupt closure and restenosis. Unfortunately, even when the implantation of the stent is accompanied by aggressive and precise antiplatelet and anticoagulation therapy (typically by systemic administration), the incidence of thrombotic vessel closure or other thrombotic complication remains significant, and the prevention of restenosis is not as successful as desired. Furthermore, an undesirable side effect of the systemic antiplatelet and anticoagulation therapy is an increased incidence of bleeding complications, most often at the percutaneous entry site.

Other conditions and diseases are treatable with stents, catheters, cannulae and other devices inserted into the esophagus, trachea, colon, biliary tract, urinary tract and other locations in the body, or with orthopedic devices, implants, or replacements. It would be desirable to develop devices and methods for reliably delivering suitable agents, drugs or bioactive materials directly into a body portion during or following a medical procedure, so as to treat or prevent such conditions and diseases, for example, to prevent abrupt closure and/or restenosis of a body portion such as a passage, lumen or blood vessel. As a particular example, it would be desirable to have devices and methods which can deliver an antithrombic or other medication to the region of a blood vessel which has been treated by PTA, or by another interventional technique such as atherectomy, laser ablation, or the like. It would also be desirable that such devices would deliver their agents over both the short term (that is, the initial hours and days after treatment) and the long term (the weeks and months after treatment). It would also be desirable to provide precise control over the delivery rate for the agents, drugs or bioactive materials, and to limit systemic exposure to them. This would be particularly advantageous in therapies involving the delivery of a chemotherapeutic agent to a particular organ or site through an intravenous catheter (which itself has the advantage of reducing the amount of agent needed for successful treatment), by preventing stenosis both along the catheter and at the catheter tip. A wide variety of other therapies could be similarly improved. Of course, it would also be desirable to avoid degradation of the agent, drug or bioactive material during its incorporation on or into any such device.

SUMMARY OF THE INVENTION

The foregoing problems are solved and a technical advance is achieved in an illustrative vascular stent or other implantable medical device that provides a controlled release of an agent, drug or bioactive material into the vascular or other system, or other location in the body, in which a stent or other device is positioned. Applicants have discovered that the degradation of an agent, a drug or a bioactive material that is applied to such a device can be avoided by positing a coating layer on one surface of the device structure. The agent, drug or bioactive material is posited over at least a portion of the coating layer, wherein the coating layer provides for a controlled release of the bioactive material posited thereon. Furthermore, the medical device further includes a porous layer positioned over the bioactive material wherein the porous layer is composed of a polymer and the polymer provides for a controlled release of the bioactive material through the porous layer.

In one aspect, the coating layer comprises a non-porous material of for example a parylene derivative. This coating layer has a thickness preferably in a range from 50 to 500,000 Angstroms, more preferably in a range from 100,000 to 500,000 Angstroms, and illustratively approximately 200,000 Angstroms. In another aspect, the non-porous material is either an adsorbent or an absorbent material, where the coating layer of the adsorbent material has a thickness of approximately 230,000 Angstroms.

In another aspect of the invention, the bioactive material layer includes a chimeric monoclonal antibody such as an antiplatelet GP IIb/IIIa antibody.

In still another aspect of the invention, an adhesive promotion layer is posited on one surface of the structure on which the coating layer is posited over at least a portion thereof. Preferably the adhesion promotion layer includes silane having a thickness in range of 0.5 to 5,000 Angstroms.

Applicants have also discovered that the degradation of an agent, a drug or a bioactive material applied to such a device may be avoided by covering the agent, drug or bioactive material with a porous layer of a biocompatible polymer that is applied without the use of solvents, catalysts, heat or other chemicals or techniques, which would otherwise be likely to degrade or damage the agent, drug or material. Those biocompatible polymers may be applied preferably by vapor deposition or plasma deposition, and may polymerize and cure merely upon condensation from the vapor phase, or may be photolytically polymerizable and are expected to be useful for this purpose. However, it should be recognized that other coating techniques may also be employed.

Preferably, when the device is intended for use in the vascular system, the bioactive material in the at least one layer is heparin or another antiplatelet or antithrombotic agent, or dexamethasone, dexamethasone acetate, dexamethasone sodium phosphate, or another dexamethasone derivative or anti-inflammatory steroid. Furthermore, a wide range of other bioactive materials can be employed, including, but not limited to, the following categories of agents: thrombolytics, vasodilators, antihypertensive agents, antimicrobials or antibiotics, antimitotics, antiproliferatives, antisecretory agents, non-steroidal anti-inflammatory drugs, immunosuppressive agents, growth factors and growth factor antagonists, antitumor and/or chemotherapeutic agents, antipolymerases, antiviral agents, photodynamic therapy agents, antibody targeted therapy agents, prodrugs, sex hormones, free radical scavengers, antioxidants, biologic agents, radiotherapeutic agents, radiopaque agents and radiolabelled agents. The major restriction is that the bioactive material must be able to withstand the coating techniques, for example, the vacuum employed during vapor deposition or plasma deposition of the at least one porous layer. In other words, the bioactive material must have a relatively low vapor pressure at the deposition temperature, typically, near or at room temperature.

In a preferred aspect of the present invention, the bioactive material is an immunosuppressive agent comprising azathioprine or azathioprine sodium; basiliximab; cyclosporin or cyclosporine (cyclosporin A); daclizumab (dacliximab); glatiramer or glatiramer acetate; muromonab-CD3; mycophenolate, mycophenolate mofetil (MMF), mycophenolate morpholinoethyl or mycophenolic acid; tacrolimus (FK506), anhydrous tacrolimus or tacrolimus monohydrate; sirolimus; interferon alfa-2a, recombinant (rIFN-A or IFLrA); antilymphocyte immunoglobulin (ALG), antithymocyte immunoglobulin (ATG), antilymphocyte serum, antithymocyte serum, lymphocytic antiserum or thymitic antiserum; brequinar or brequinar sodium; cyclophosphamide, cyclophosphamide monohydrate or anhydrous cyclophosphamide; dactinomycin, actinomycin C, actinomycin D or meractinomycin; daunorubicin, daunorubicin hydrochloride, daunomycin hydrochloride or rubidomycin hydrochloride; doxorubicin, doxorubicin hydrochloride, adriamycin or adriamycin hydrochloride; fluorouracil; gusperimus or gusperimus hydrochloride; inolimomab; leflunomide; mercaptopurine, mercaptopurine monohydrate, purinethiol or anhydrous mercaptopurine; methotrexate, methotrexate sodium, methotrexate disodium, alpha-methopterin or amethopterin; mustine, mustine hydrochloride, chlormethine hydrochloride, chlorethazine hydrochloride, mechlorethamine hydrochloride or nitrogen mustard (mustine); mizoribine; vinblastine, vinblastine sulfate or vincaleukoblastine sulphate; a pharmacologically or physiologically acceptable salt of any of the foregoing; or a pharmacologically or physiologically acceptable mixture of any two or more of the foregoing.

In another preferred aspect of the present invention, the bioactive material is an immunosuppressive agent comprising capecitabine; carmofur; epirubicin or epirubicin hydrochloride; idarubicin or idarubicin hydrochloride; mafosfamide; menogaril; mitozantrone, mitozantrone hydrochloride or mitoxantrone hydrochloride; pirarubicin or tepirubicin; piroxantrone, piroxantrone hydrochloride, anthrapyrazole hydrochloride or oxantrazole hydrochloride; teloxantrone or teloxantrone hydrochloride; thioguanine, anhydrous thioguanine, thiguanine hemihydrate or tioguanine; trofosfamide, trilophosphamide or trophosphamide; uramustine or uracil mustard; vincristine, vincristine sulphate or leurocristine sulphate; vindesine, vindesine sulfate or desacetyl vinblastine amide sulfate; vinorelbine, vinorelbine tartrate or vinorelbine ditartrate; zorubicin or zorubicin hydrochloride; a pharmacologically or physiologically acceptable salt of any of the foregoing; or a pharmacologically or physiologically acceptable mixture of any two or more of the foregoing.

The properties of these actual and expected immunosuppressive agents are described in more detail below. Of course, several of these immunosuppressive agents are members of others of the categories of bioactive materials identified above, as any particular material may have a range of pharmacological or physiological effects. The categories should be taken as descriptive, not limiting.

The at least one porous layer is preferably composed of a polyamide, parylene or a parylene derivative applied by catalyst-free vapor deposition and is conveniently about 5,000 to 250,000 Å thick, which is adequate to provide a controlled release of the bioactive material. "Parylene" is both a generic name for a known group of polymers based on p-xylylene and made by vapor phase polymerization, and a name for the unsubstituted form of the polymer; the latter usage is employed herein. More particularly, parylene or a parylene derivative is created by first heating p-xylene or a suitable derivative at an appropriate temperature (for example, at about 950° C.) to produce the cyclic dimer di-p-xylylene (or a derivative thereof). The resultant solid can be separated in pure form, and then cracked and pyrolyzed at an appropriate temperature (for example, at about 680° C.) to produce a monomer vapor of p-xylylene (or derivative); the monomer vapor is cooled to a suitable temperature (for example, below 50° C.) and allowed to condense on the desired object, for example, on the at least one layer of bioactive material. The resultant polymer has the repeating structure $(CH_2C_6H_4CH_2)_n$, with n equal to about 5,000, and a molecular weight in the range of 500,000.

As indicated, parylene and parylene derivative coatings applicable by vapor deposition are known for a variety of biomedical uses, and are commercially available from or through a variety of sources, including Specialty Coating Systems (100 Deposition Drive, Clear Lake, Wis. 54005), Para Tech Coating, Inc. (35 Argonaut, Aliso Viejo, Calif. 92656) and Advanced Surface Technology, Inc. (9 Linnel Circle, Billerica, Mass. 01821-3902).

The at least one porous layer can alternatively be applied by plasma deposition. Plasma is an ionized gas maintained under vacuum and excited by electrical energy, typically in the radiofrequency range. Because the gas is maintained under vacuum, the plasma deposition process occurs at or near room temperature. Plasma can be used to deposit polymers such as poly(ethylene oxide), poly(ethylene glycol), and poly(propylene oxide), as well as polymers of silicone, methane, tetrafluoroethylene (including TEFLON brand polymers), tetramethyldisiloxane, and others.

While the foregoing represents some preferred embodiments of the present invention, other polymer systems may also be employed, e.g., polymers derived from photopolymerizeable monomers. Also, other coating techniques may be utilized, e.g., dipping, spraying, and the like.

The device may include two or more layers of different bioactive materials atop the structure. However, for the purposes of the present invention, the same bioactive material will generally not be posited on the different surfaces of the device within the same layer. In other words, each surface of the device structure will carry a different bioactive material or materials except where the bioactive material is the innermost or outermost layer, e.g. heparin may form the innermost layer or the outermost layer or both. These additional layers may be placed directly atop one another or can be separated by additional porous polymer layers between each of them. Additionally, the layers of bioactive materials can comprise a mixture of different bioactive materials. The porous layers are also preferably composed of parylene or a parylene derivative. Advantageously, the two or more bioactive materials can have different solubilities, and the layer containing the less soluble bioactive material (for example, dexamethasone) is preferably posited above the layer containing the more soluble bioactive material (for example, heparin). Unexpectedly, this has been found to increase the in vitro release rate of some relatively less soluble materials such as dexamethasone, while simultaneously decreasing the release rate of some relatively more soluble materials such as heparin.

While the structure included in the device may be configured in a variety of ways, the structure is preferably configured as a vascular stent composed of a biocompatible metal such as stainless steel, nickel, silver, platinum, gold, titanium, tantalum, iridium, tungsten, Nitinol, inconel, or the like. An additional substantially nonporous coating layer of parylene or a parylene derivative or other biocompatible polymer of about 50,000 to 500,000 Å thick may be posited directly atop the vascular stent, beneath the at least one layer of bioactive material. The additional coating layer can merely be relatively less porous than the at least one porous layer, but preferably is substantially nonporous, that is, sufficiently nonporous to render the stent essentially impervious to blood during normal circumstances of use.

Any of a wide variety of stents can be employed in the present invention as the structure having a layer of bioactive material posited on it. Stents useful in the practice of the present invention include self-expanding stents, balloon-expanded stents or even stents already in an expanded condition. Such a stent can be of any desired configuration, for example, any one of the three principal styles presently in use: filamentous or strand type (single or plural), rolled sheet type or laser-cut tube or cannula. The details of these styles of stent are contained in the various patents identified below. The usefulness of the present invention is of course not limited to these types of stents or the particular stents shown in the patents incorporated below.

In a preferred aspect, then, the present invention is directed to an implantable medical device, comprising a structure adapted for introduction into a patient, the structure having at least one surface; at least one layer of an immunosuppressive agent posited over the at least one surface of the structure; and at least one porous layer posited over the at least one layer of an immunosuppressive agent.

In another preferred aspect, the present invention is directed to a medical device comprising a stent adapted for introduction into a patient, the stent having at least one surface; at least one layer of an immunosuppressive agent posited over the at least one surface of the stent; and at least one porous layer posited over the at least one layer of an immunosuppressive agent.

In a further preferred aspect, the present invention is directed to an expandable, self-expanding or expanded stent including a base material, wherein at least one hole or well is formed in the base material of the stent, the at least one hole or well containing an immunosuppressive agent applied therein.

In each of these three aspects of the present invention, the preferred immunosuppressive agents are those listed above. The porous layer, if present, provides for a controlled release of the immunosuppressive agent through the porous layer. The structure or stent can include at least one coating layer posited over the at least one surface of the structure or stent, the immunosuppressive agent being posited over the coating layer and adsorbed on it or absorbed into it, such that the coating layer provides for a controlled release of the immunosuppressive agent. The surface of the structure or stent can have a base material having at least one hole, well, groove or slot in which the immunosuppressive agent is contained. The immunosuppressive agent is preferably defined as above.

The device and methods of the present invention are useful in a wide variety of locations within a human or veterinary patient, such as in the esophagus, trachea, colon, biliary tract, urinary tract and vascular system, as well as for subdural and orthopedic devices, implants or replacements. They are particularly advantageous for reliably delivering suitable bioactive materials during or following an intravascular procedure, and find particular use in preventing abrupt closure and/or restenosis of a blood vessel. More particularly, they permit, for example, the delivery of an antithrombotic, an antiplatelet, an anti-inflammatory steroid, or another medication to the region of a blood vessel which has been opened by PTA. Likewise, it allows for the delivery of one bioactive material to, for example, the lumen of a blood vessel and another bioactive material to the vessel wall. The use of a porous polymer layer permits the release rate of a bioactive material to be carefully controlled over both the short and long terms.

These and other aspects of the present invention will be appreciated by those skilled in the art upon the reading and understanding of the specification.

In another aspect of the invention, the bioactive material is attached to the non-porous layer and is advantageously eluted for prolonged periods of time. The non-porous layer is attached to the base material of the structure. The non-porous layer can be any of those previously or subsequently listed herein, and, likewise, the bioactive material can be any of those previously or subsequently listed herein. Conveniently, and in a preferred embodiment, a glycoprotein IIb/IIIa inhibitor such as commercially available ReoPro™ is attached to a non-porous layer of parylene positioned on the outer surface of the medical device such as a coronary stent. The ReoPro™ is advantageously eluted from the surface of the stent for prolonged periods of time.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which.

DETAILED DESCRIPTION OF THE PREFERRED EMBODIMENTS

Figure 1:
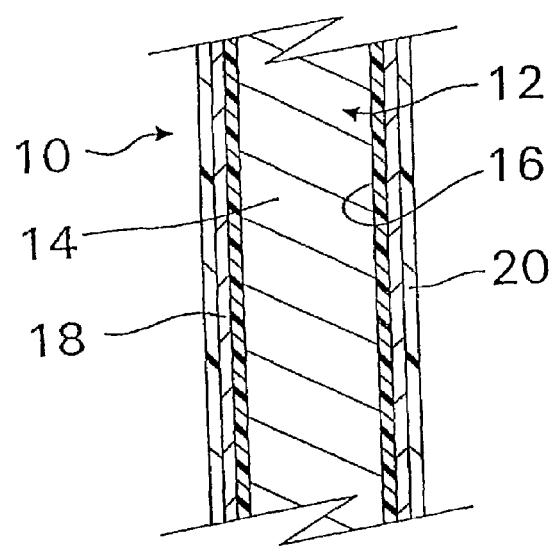
FIG. 1 is a cross-sectional view of a first preferred embodiment of the present invention.

With reference now to FIG. 1, an implantable medical device 10 in accordance with the present invention is shown and first comprises a structure 12 adapted for introduction into a human or veterinary patient. "Adapted" means that the structure 12 is shaped and sized for such introduction. For clarity, only a portion of the structure 12 is shown in FIG. 1.

By way of example, the structure 12 is configured as a vascular stent particularly adapted for insertion into the vascular system of the patient. However, this stent structure can be used in other systems and sites such as the esophagus, trachea, colon, biliary ducts, urethra and ureters, subdural among others. Indeed, the structure 12 can alternatively be configured as any conventional vascular or other medical device, and can include any of a variety of conventional stents or other adjuncts, such as helical wound strands, perforated cylinders, or the like. Moreover, because the problems addressed by the present invention arise with respect to those portions of the device actually positioned within the patient, the inserted structure 12 need not be an entire device, but can merely be that portion of a vascular or other device which is intended to be introduced into the patient. Accordingly, the structure 12 can be configured as at least one of, or any portion of, a catheter, a wire guide, a cannula, a stent, a vascular or other graft, a cardiac pacemaker lead or lead tip, a cardiac defibrillator lead or lead tip, a heart valve, or an orthopedic device, appliance, implant, or replacement. The structure 12 can also be configured as a combination of portions of any of these.

Most preferably, however, the structure 12 is configured as a vascular stent such as the commercially available Gianturco-Roubin FLEX-STENT® or GR II™ coronary stent from Cook Incorporated, Bloomington, Ind. Such stents are typically about 10 to about 60 mm in length and designed to expand to a diameter of about 2 to about 6 mm when inserted into the vascular system of the patient. The Gianturco-Roubin stent in particular is typically about 12 to about 25mm in length and designed to expand to a diameter of about 2 to about 4 mm when so inserted.

These stent dimensions are, of course, applicable to exemplary stents employed in the coronary arteries. Structures such as stents or catheter portions intended to be employed at other sites in the patient, such as in the aorta, esophagus, trachea, colon, biliary tract, or urinary tract will have different dimensions more suited to such use. For example, aortic, esophageal, tracheal and colonic stents may have diameters up to about 25 mm and lengths about 100 mm or longer.

The structure 12 is composed of a base material 14 suitable for the intended use of the structure 12. The base material 14 is preferably biocompatible, although cytotoxic or other poisonous base materials may be employed if they are adequately isolated from the patient. Such incompatible materials may be useful in, for example, radiation treatments in which a radioactive material is positioned by catheter in or close to the specific tissues to be treated. Under most circumstances, however, the base material 14 of the structure 12 should be biocompatible.

A variety of conventional materials can be employed as the base material 14. Some materials may be more useful for structures other than the coronary stent exemplifying the structure 12. The base material 14 may be either elastic or inelastic, depending upon the flexibility or elasticity of the polymer layers to be applied over it. The base material may be either biodegradable or non-biodegradable, and a variety of biodegradable polymers are known. Moreover, some biologic agents have sufficient strength to serve as the base material 14 of some useful structures 12, even if not especially useful in the exemplary coronary stent.

Accordingly, the base material 14 can include at least one of stainless steel, tantalum, titanium, nitinol, gold, platinum, inconel, iridium, silver, tungsten, or another biocompatible metal, or alloys of any of these; carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these. Stainless steel is particularly useful as the base material 14 when the structure 12 is configured as a vascular stent.

Of course, when the structure 12 is composed of a radiolucent material such as polypropylene, polyethylene, or others above, a conventional radiopaque coating may and preferably should be applied to it. The radiopaque coating provides a means for identifying the location of the structure 12 by X-ray or fluoroscopy during or after its introduction into the patient's vascular system.

With continued reference to FIG. 1, the vascular device 10 of the present invention next comprises at least one layer 18 of a bioactive material posited on one surface of the structure 12. For the purposes of the present invention, at least one bioactive material is posited on one surface of the structure 12, and the other surface will either contain no bioactive material or one or more different bioactive materials. In this manner, one or more bioactive materials or drugs may be delivered, for example, with a vascular stent, to the blood stream from the lumen surface of the stent, and a different treatment may be delivered on the vessel surface of the stent. A vast range of drugs, medicaments and materials may be employed as the bioactive material in the layer 18, so long as the selected material can survive exposure to the vacuum drawn during vapor deposition or plasma deposition. Particularly useful in the practice of the present invention are materials which prevent or ameliorate abrupt closure and restenosis of blood vessels previously opened by stenting surgery or other procedures. Thrombolytics (which dissolve, break up or disperse thrombi) and antithrombogenics (which interfere with or prevent the formation of thrombi) are especially useful bioactive materials when the structure 12 is a vascular stent. Particularly preferred thrombolytics are urokinase, streptokinase, and the tissue plasminogen activators. Particularly preferred antithrombogenics are heparin, hirudin, and the antiplatelets.

Urokinase is a plasminogen activating enzyme typically obtained from human kidney cell cultures. Urokinase catalyzes the conversion of plasminogen into the fibrinolytic plasmin, which breaks down fibrin thrombi.

Heparin is a mucopolysaccharide anticoagulant typically obtained from porcine intestinal mucosa or bovine lung. Heparin acts as a thrombin inhibitor by greatly enhancing the effects of the blood's endogenous antithrombin III. Thrombin, a potent enzyme in the coagulation cascade, is key in catalyzing the formation of fibrin. Therefore, by inhibiting thrombin, heparin inhibits the formation of fibrin thrombi. Alternatively, heparin may be covalently bound to the outer layer of structure 12. Thus, heparin would form the outermost layer of structure 12 and would not be readily degraded enzymatically, and would remain active as a thrombin inhibitor.

Of course, bioactive materials having other functions can also be successfully delivered by the device 10 of the present invention. For example, an antiproliferative agent such as methotrexate will inhibit over-proliferation of smooth muscle cells and thus inhibit restenosis of the dilated segment of the blood vessel. The antiproliferative is desirably supplied for this purpose over a period of about four to six months. Additionally, localized delivery of an antiproliferative agent is also useful for the treatment of a variety of malignant conditions characterized by highly vascular growth. In such cases, the device 10 of the present invention could be placed in the arterial supply of the tumor to provide a means of delivering a relatively high dose of the antiproliferative agent directly to the tumor.

A vasodilator such as a calcium channel blocker or a nitrate will suppress vasospasm, which is common following angioplasty procedures. Vasospasm occurs as a response to injury of a blood vessel, and the tendency toward vasospasm decreases as the vessel heals. Accordingly, the vasodilator is desirably supplied over a period of about two to three weeks. Of course, trauma from angioplasty is not the only vessel injury which can cause vasospasm, and the device 10 may be introduced into vessels other than the coronary arteries, such as the aorta, carotid arteries, renal arteries, iliac arteries or peripheral arteries for the prevention of vasospasm in them.

A variety of other bioactive materials are particularly suitable for use when the structure 12 is configured as something other than a coronary stent. For example, an anti-cancer chemotherapeutic agent can be delivered by the device 10 to a localized tumor. More particularly, the device 10 can be placed in an artery supplying blood to the tumor or elsewhere to deliver a relatively high and prolonged dose of the agent directly to the tumor, while limiting systemic exposure and toxicity. The agent may be a curative, a pre-operative debulker reducing the size of the tumor, or a palliative which eases the symptoms of the disease. It should be noted that the bioactive material in the present invention is delivered across the device 10, and not by passage from an outside source through any lumen defined in the device 10, such as through a catheter employed for conventional chemotherapy. The bioactive material of the present invention may, of course, be released from the device 10 into any lumen defined in the device, or to tissue in contact with the device and that the lumen may carry some other agent to be delivered through it. For example, tamoxifen citrate, Taxol® or derivatives thereof Proscar®, Hytrin®, or Eulexin® may be applied to the tissue-exposed surface of the device for delivery to a tumor located, for example, in breast tissue or the prostate.

Dopamine or a dopamine agonist such as bromocriptine mesylate or pergolide mesylate is useful for the treatment of neurological disorders such as Parkinson's disease. The device 10 could be placed in the vascular supply of the thalamic substantia nigra for this purpose, or elsewhere, localizing treatment in the thalamus.

A wide range of other bioactive materials can be delivered by the device 10. Accordingly, it is preferred that the bioactive material contained in the layer 18 includes at least one of heparin, covalent heparin, or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; Hytrin® or other antihypertensive agents; an antimicrobial agent or antibiotic; aspirin, ticlopidine, a glycoprotein IIb/IIIa inhibitor or another inhibitor of surface glycoprotein receptors, or another antiplatelet agent; colchicine or another antimitotic, or another microtubule inhibitor, dimethyl sulfoxide (DMSO), a retinoid or another antisecretory agent; cytochalasin or another actin inhibitor; or a remodelling inhibitor; deoxyribonucleic acid, an antisense nucleotide or another agent for molecular genetic intervention; methotrexate or another antimetabolite or antiproliferative agent; tamoxifen citrate, Taxol® or the derivatives thereof, or other anti-cancer chemotherapeutic agents; dexamethasone, dexamethasone sodium phosphate, dexamethasone acetate or another dexamethasone derivative, or another anti-inflammatory steroid or non-steroidal antiinflammatory agent; cyclosporin or another immunosuppressive agent; trapidal (a PDGF antagonist), angiopeptin (a growth hormone antagonist), angiogenin, a growth factor or an anti-growth factor antibody, or another growth factor antagonist; dopamine, bromocriptine mesylate, pergolide mesylate or another dopamine agonist; $^{60}$Co (5.3 year half life), $^{192}$Ir (73.8 days), $^{32}$P (14.3 days), $^{111}$In (68 hours), $^{90}$Y (64 hours), $^{99m}$Tc (6 hours) or another radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alpha tocopherol, superoxide dismutase, deferoxamine, a 21-aminosteroid (lasaroid) or another free radical scavenger, iron chelator or antioxidant; a $^{14}$C-, $^{3}$H-, $^{131}$I-, $^{32}$P- or $^{36}$S-radiolabelled form or other radiolabelled form of any of the foregoing; estrogen or another sex hormone; AZT or other antipolymerases; acyclovir, famciclovir, rimantadine hydrochloride, ganciclovir sodium, Norvir, Crixivan, or other antiviral agents; 5-aminolevulinic acid, meta-tetrahydroxyphenylchlorin, hexadecafluoro zinc phthalocyanine, tetramethyl hematoporphyrin, rhodamine 123 or other photodynamic therapy agents; an IgG2 Kappa antibody against Pseudomonas aeruginosa exotoxin A and reactive with A431 epidermoid carcinoma cells, monoclonal antibody against the noradrenergic enzyme dopamine beta-hydroxylase conjugated to saporin or other antibody targeted therapy agents; gene therapy agents; and enalapril and other prodrugs; Proscar®, Hytrin® or other agents for treating benign prostatic hyperplasia (BHP) or a mixture of any of these; and various forms of small intestine submucosa (SIS).

A wide variety of known immunosuppressive agents are expected to be useful as bioactive materials in the practice of the present invention. More specifically, useful immunosuppressive agents include azathioprine or azathioprine sodium, an imidazoyl derivative of 6-mercaptopurine (6-MP) and its sodium salt; basiliximab, a chimeric (murine/human) monoclonal antibody, in particular, an interleukin-2 (IL-2) receptor antagonist or anti-interleukin-2 receptor (CD25) antibody; cyclosporin or cyclosporine (cyclosporin A), a cyclic polypeptide consisting of 11 amino acids, produced as a metabolite of the fungus species *Beauveria nivea* (=*Tolypocladium inflatum* Gams; daclizumab (dacliximab), a humanized IgG$_1$ monoclonal antibody produced by recombinant DNA technology that binds specifically to the alpha subunit (Tac subunit) of the human high-affinity interleukin-2 (IL-2) receptor (anti-interlukin-2-receptor antibody), a composite of 90% human and 10% murine antibody sequences; glatiramer or glatiramer acetate, a random synthetic copolymer of L-alanine, L-glutamic acid, L-lysine and L-tyrosine, in a molar ratio of 6:1.9:4.7:1, and its acetate; muromonab-CD3, a murine monoclonal antibody to the T3 (CD3) antigen of human T-cells, more particularly, a biochemically purified IgG$_{2a}$ immunoglobulin; mycophenolate, mycophenolate mofetil (MMF), mycophenolate morpholinoethyl or mycophenolic acid (mycophenolate hydrolyzes to form an active metabolite (MPA), a potent, selective, uncompetitive and reversible inhibitor of inosine monophosphate dehydrogenase; mycophenolic acid is derived from *Penicillium stoloniferum*); tacrolimus (FK506), anhydrous tacrolimus or tacrolimus monohydrate, a macrolide immunosuppressant produced by *Streptomyces tsukubaensis* which inhibits T-lymphocyte activation; sirolimus, a macrolide immunosuppressive agent also obtained from *Streptomyces tsukubaensis* which inhibits both T-lymphocyte activation and proliferation that occurs in response to antigenic and cytokine (interleukin [IL]-2, IL-4 and IL-5) stimulation, and also inhibits antibody production; interferon alfa-2a, recombinant (rIFN-A or IFLrA), a highly purified, sterile protein containing 165 amino acids, manufactured by recombinant DNA technology that employs a genetically engineered *Escherichia coli* bacterium; antilymphocyte immunoglobulin (ALG) or antithymocyte immunoglobulin (ATG), polyclonal antibodies to human lymphocytes produced by the purification of sera from appropriately immunized animals such as horses, rabbits and goats (ALG implies a product raised against all lymphocyte subsets, while ATG implies specificity for T-cells, either thymus lymphocytes or thymocytes), as well as their native sera (antilymphocyte serum and antithymocyte serum, respectively, sometimes referred to as lymphocytic antiserum and thymitic antiserum, respectively); brequinar or brequinar sodium, an inhibitor of pyrimidine metabolism; cyclophosphamide, cyclophosphamide monohydrate or anhydrous cyclophosphamide, an antineoplastic that is converted in the body to an active alkylating metabolite with properties similar to those of mustine; dactinomycin, actinomycin C, actinomycin D or meractinomycin, an antibiotic produced by the growth of *Streptomyces chrysomallus* and other species of *Streptomyces*; daunorubicin, daunorubicin hydrochloride, daunomycin hydrochloride or rubidomycin hydrochloride, an antineoplastic anthracycline antibiotic produced by *Streptomyces coeruleorubidus* or *S. peucetius*, and its hydrochloride; doxorubicin, doxorubicin hydrochloride, adriamycin or adriamycin hydrochloride, an anthracycline antineoplastic antibiotic isolated from certain strains of *Streptomyces coeruleorubidus* or *S. peucetius*, and its hydrochloride; fluorouracil, a pyrimidine analogue, in particular an antineoplastic that acts as an antimetabolite to uracil; gusperimus or gusperimus hydrochloride, a guanidine derivative and its hydrochloride; inolimomab, a murine antihuman monoclonal antibody directed against the alpha-chain of the interleukin-2 receptor (CD25); leflunomide, having immunosuppressant properties believed to be partly due to the action of its active metabolite A77-1726 in inhibiting pyrimidine synthesis; mercaptopurine, mercaptopurine monohydrate, purinethiol or anhydrous mercaptopurine, an antineoplastic that acts as an antimetabolite; methotrexate, methotrexate sodium, methotrexate disodium, alpha-methopterin or amethopterin, a mixture of 4-amino-10-methylfolic acid and related substances, or the sodium salts thereof, acting as an antimetabolite of folic acid; mustine, mustine hydrochloride, chlormethine hydrochloride, chlorethazine hydrochloride, mechlorethamine hydrochloride or nitrogen mustard (mustine), an alkylating agent; mizoribine, 5-hydroxy-1-beta-D-ribofuranosylimidazole-4-carboxamide; vinblastine, vinblastine sulfate or vincaleukoblastine sulphate, an alkaloid (vincaleukoblastine) extracted from *Vinca rosea* (*Catharanthus roseus*) (Apocynaceae), or a suflate thereof; pharmacologically or physiologically acceptable salts of any of the foregoing; and pharmacologically or physiologically acceptable mixtures of any two or more of the foregoing.

Other immunosuppressive agents are expected to be useful as well, some more useful than others, as is common with bioactive materials. Any experimentation in this regard would appear to be commensurate with the degree of experimentation normally encountered when initially contemplating the use of materials from the other categories of bioactive materials mentioned above.

It should be noted that sirolimus may be particularly advantageous in the practice of the present invention, in that it appears to be cytostatic with respect to the smooth muscle cells of the arterial walls, and in that its inhibition of the mammalian target of rapamycin (mTOR) suppresses cytokine-driven T-cell proliferation.

In addition to these immunosuppressive agents, other materials having structural, pharmacological or physiological properties comparable to those of known immunosuppressive agents may be expected to be useful as immunosuppressive agents in the practice of the present invention. Such materials include capecitabine, a fluoropyrimidine prodrug that is converted in the body to fluorouracil when orally administered; carmofur, a derivative of fluorouracil which has been described as having similar antineoplastic actions; epirubicin or epirubicin hydrochloride, an anthracycline antibiotic with antineoplastic actions similar to those of doxorubicin; idarubicin or idarubicin hydrochloride, an anthracycline antibiotic with antineoplastic actions similar to those of doxorubicin; mafosfamide, a derivative of cyclophosphamide that has been used to treat bone marrow for transplantation; menogaril, an anthracycline derivative related to doxorubicin but which may not act by intercalation of DNA; mitozantrone, mitozantrone hydrochloride or mitoxantrone hydrochloride, an antineoplastic structurally related to doxorubicin, or its hydrochloride; pirarubicin or tepirubicin, an anthracycline antibiotic antineoplastic which is a structural analogue of doxorubicin; piroxantrone, piroxantrone hydrochloride, anthrapyrazole hydrochloride or oxantrazole hydrochloride, which like mitozantrone is a structural analogue of the anthracycline antibiotics, and its hydrochlorides; teloxantrone or teloxantrone hydrochloride, an anthrapyrazole derivative with structural similarities to mitozantrone; thioguanine, anhydrous thioguanine, thiguanine hemihydrate or tioguanine, an analogue of a naturally occurring purine (guanine) and is an antineoplastic with actions and uses similar to those of mercaptopurine; trofosfamide, trilophosphamide or trophosphamide, a derivative of cyclophosphamide described as having the same general properties; uramustine or uracil mustard, an antineoplastic agent derived from mustine and described as having a similar mode of action; vincristine, vincristine sulphate or leurocristine sulphate, an alkaloid (22-oxovincaleukoblastine) obtained from *Vinca rosea* (*Catharanthus roseus*) (Apocynaceae), or sulfate thereof, which may act similarly to vinblastine; vindesine, vindesine sulfate or desacetyl vinblastine amide sulfate, an antineoplastic agent derived from vinblastine, or a sulfate thereof; vinorelbine, vinorelbine tartrate or vinorelbine ditartrate, a semisynthetic derivative of vinblastine described as having similar general properties, or a tartrate thereof; zorubicin or zorubicin hydrochloride, an anthracycline antibiotic or hydrochloride thereof with antineoplastic actions similar to those of doxorubicin; pharmacologically or physiologically acceptable salts of any of the foregoing; and pharmacologically or physiologically acceptable mixtures of any two or more of the foregoing.

The foregoing lists of actual and expected immunosuppressive agents should not be taken as exhaustive. Further, those skilled in the art will immediately recognize that some of the listed materials share one or more properties of the other categories of bioactive materials identified above. Identifying the listed materials as actual or expected immunosuppressive agents should not be taken to exclude their being considered as members of one or more of those other categories of bioactive materials. For example, several of the identified immunosuppressive agents are noted above to have antiproliferative effects; these agents can be employed in the present invention for either or both of their immunosuppressive and antiproliferative effects.

In a particularly preferred aspect, the layer of bioactive material contains preferably from about 0.01 mg to about 10 mg and more preferably from about 0.1 mg to about 4 mg of the bioactive material per $cm^2$ of the gross surface area of the structure. "Gross surface area" refers to the area calculated from the gross or overall extent of the structure, and not necessarily to the actual surface area of the particular shape or individual parts of the structure. In other terms, about 100 μg to about 300 μg of drug per 0.001 inch of coating thickness may be contained on the device surface.

When the structure 12 is configured as a vascular stent, particularly preferred materials for the bioactive material of the layer 18 are heparin, anti-inflammatory steroids including but not limited to dexamethasone and its derivatives, and mixtures of heparin and such steroids. Immunosuppressive agents such as those identified above are also particularly preferred materials for the bioactive material of the layer 18 when the structure 12 is configured as a vascular stent.

Still with reference to FIG. 1, the device 10 of the present invention also comprises at least one porous layer 20 posited over the layer 18 of bioactive material and the bioactive-material-free surface. The purpose of the porous layer 20 is to provide a controlled release of the bioactive material when the device 10 is positioned in the vascular system of a patient. The thickness of the porous layer 20 is chosen so as to provide such control.

More particularly, the porous layer 20 is composed of a polymer deposited on the bioactive material layer 18, preferably by vapor deposition. Plasma deposition may also be useful for this purpose. Preferably, the layer is one that is polymerized from a vapor which is free of any solvent, catalysts or similar polymerization promoters. Also preferably, the polymer in the porous layer 20 is one which automatically polymerizes upon condensation from the vapor phase, without the action of any curative agent or activity such as heating, the application of visible or ultraviolet light, radiation, ultrasound, or the like. Most preferably, the polymer in the porous layer 20 is polyimide, parylene or a parylene derivative.

When first deposited, the parylene or parylene derivative is thought to form a network resembling a fibrous mesh, with relatively large pores. As more is deposited, the porous layer 20 not only becomes thicker, but it is believed that parylene or parylene derivative is also deposited in the previously formed pores, making the existing pores smaller. Careful and precise control over the deposition of the parylene or parylene derivative therefore permits close control over the release rate of material from the at least one layer 18 of bioactive material. It is for this reason that the bioactive material lies under the at least one porous layer 20, rather than being dispersed within or throughout it. The porous layer 20, however, also protects the bioactive material layer 18 during deployment of the device 10, for example, during insertion of the device 10 through a catheter and into the vascular system or elsewhere in the patient.

As shown in FIG. 1, the device 10 of the present invention can further comprise at least one additional coating layer 16 posited between the structure 12 and the at least one layer 18 of bioactive material. While the additional coating layer 16 can simply be a medical grade primer, the additional coating layer 16 is preferably composed of the same polymer as the at least one porous layer 20. However, the additional coating layer 16 is also preferably less porous than the at least one porous layer 20, and is more preferably substantially nonporous. "Substantially nonporous" means that the additional coating layer 16 is sufficiently impervious to prevent any appreciable interaction between the base material 14 of the structure 12 and the blood to which the device 10 will be exposed during use. The use of an additional coating layer 16 which is substantially nonporous would permit the use of a toxic or poisonous base material 14, as mentioned above. Even if the base material 14 of the structure 12 is biocompatible, however, it may be advantageous to isolate it from the blood by use of a substantially nonporous coating layer 16.

Other polymer systems that may find application within the scope of the invention include polymers derived from photopolymerizable monomers such as liquid monomers preferably having at least two cross linkable C—C (Carbon to Carbon) double bonds and being a non-gaseous addition polymerizable ethylenically unsaturated compound, having a boiling point above 100° C., at atmospheric pressure, a molecular weight of about 100-1500 and being capable of forming high molecular weight addition polymers readily. More preferably, the monomer is preferably an addition photopolymerizable polyethylenically unsaturated acrylic or methacrylic acid ester containing two or more acrylate or methacrylate groups per molecule or mixtures thereof. A few illustrative examples of such multifunctional acrylates are ethylene glycol diacrylate, ethylene glycol dimethacrylate, trimethylopropane triacrylate, trimethylopropane trimethacrylate, pentaerythritol tetraacrylate or pentaerythritol tetramethacrylate, 1,6-hexanediol dimethacrylate, and diethyleneglycol dimethacrylate.

Also useful in some special instances are monoacrylates such as n-butyl-acrylate, n-butyl methacrylate, 2-ethylhexyl acrylate, lauryl-acrylate, and 2-hydroxy-propyl acrylate. Small quantities of amides of (meth)acrylic acid such as N-methylol methacrylamide butyl ether are also suitable. N-vinyl compounds such as N-vinyl pyrrolidone, vinyl esters of aliphatic monocarboxylic acids such as vinyl oleate, vinyl ethers of diols such as butanediol-1,4-divinyl ether and allyl ether and allyl ester are also suitable. Also included would be other monomers such as the reaction products of di- or polyepoxides such as butanediol-1,4-diglycidyl ether or bisphenol A diglycidyl ether with (meth)acrylic acid. The characteristics of the photopolymerizable liquid dispersing medium can be modified for the specific purpose by a suitable selection of monomers or mixtures thereof.

Other useful polymer systems include a polymer that is biocompatible and minimizes irritation to the vessel wall when the stent is implanted. The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly (glycolic acid-co-trimethylene carbonate), polyphosphoester, polyphosphoester urethane, poly(amino acids), cyanoacrylates, poly(trimethylene carbonate), poly (iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid. Also, biostable polymers with a relatively low chronic tissue response such as polyurethanes, silicones, and polyesters could be used and other polymers could also be used if they can be dissolved and cured or polymerized on the stent such as polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

While plasma deposition and vapor phase deposition may be a preferred method for applying the various coatings on the stent surfaces, other techniques may be employed. For example, a polymer solution may be applied to the stent and the solvent allowed to evaporate, thereby leaving on the stent surface a coating of the polymer and the therapeutic substance. Typically, the solution can be applied to the stent by either spraying the solution onto the stent or immersing the stent in the solution. Whether one chooses application by immersion or application by spraying depends principally on the viscosity and surface tension of the solution; however, it has been found that spraying in a fine spray such as that available from an airbrush will provide a coating with the greatest uniformity and will provide the greatest control over the amount of coating material to be applied to the stent. In either a coating applied by spraying or by immersion, multiple application steps are generally desirable to provide improved coating uniformity and improved control over the amount of therapeutic substance to be applied to the stent.

When the layer 18 of bioactive material contains a relatively soluble material such as heparin, and when the at least one porous layer 20 is composed of parylene or a parylene derivative, the at least one porous layer 20 is preferably about 5,000 to 250,000 Å thick, more preferably about 5,000 to 100,000 Å thick, and optimally about 50,000 Å thick. When the at least one additional coating layer 16 is composed of parylene or a parylene derivative, the at least one additional coating is preferably about 50,000 to 500,000 Å thick, more preferably about 100,000 to 500,000 Å thick, and optimally about 200,000 Å thick.

When the at least one layer 18 of bioactive material contains a relatively soluble material such as heparin, the at least one layer 18 preferably contains a total of about 0.1 to 4 mg of bioactive material per $cm^2$ of the gross surface area of the structure 12. This provides a release rate for the heparin (measured in vitro) which is desirably in the range of 0.1 to 0.5 $mg/cm^2$ per day, and preferably about 0.25 $mg/cm^2$ per day, under typical blood flows through vascular stents. It should be noted that the solubility of dexamethasone can be adjusted as desired, with or without the inclusion of heparin, by mixing it with one or more of its relatively more soluble derivatives, such as dexamethasone sodium phosphate.

Figure 11:
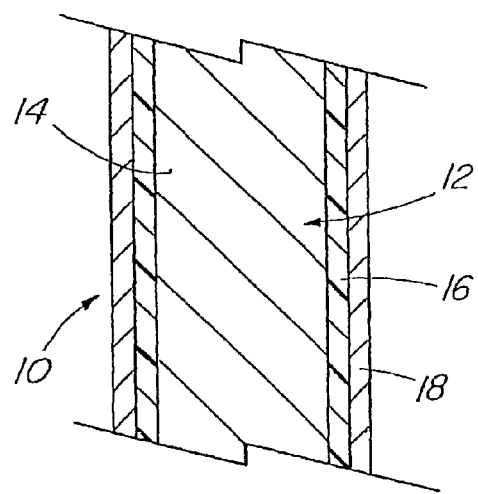
FIG. 11 depicts another aspect of the medical device of FIG. 1 utilizing a polymer coating layer with a bioactive material attached thereto.

FIG. 11 depicts another aspect of device 10 of the present invention in which coating layer 16 is applied directly to the outer surface of base material 14 of structure 12. In this configuration, coating layer 16 is preferably a non-porous coating layer as previously described. When coating layer 16 comprises a parylene derivative, non-porous coating layer 16 ranges in thickness from 50,000 to 500,000 Å, more preferably in the range of 100,000 to 500,000 Å, and optimally about 200,000 Å. In this aspect of the invention, non-porous coating layer 16 is also an adsorbent in which an adsorbent is defined as an agent that attracts other materials or particles to its surface as indicated in Dorland's Illustrated Medical Dictionary 26th Edition by W.B. Saunders Co., Philadelphia, Pa. Bioactive material 18 is then attached to the surface of coating layer 16. An additional coating layer 20 can be applied over bioactive material layer 18. Alternatively, alternating layers of coating material and the same or different bioactive materials can be applied to the surface of bioactive material layer 18. However, in this particular aspect of the invention, the outer layer of structure 12 is a bioactive material layer 18.

In still another aspect of the present invention as depicted in FIG. 11, coating layer 16 can be considered an adsorbent layer and/or an absorbent layer in which a bioactive material is attached thereto. In one particular example, device 10 is a stainless steel GR II™ stent in which the stainless steel base material 14 of structure 12 is coated with a polymer and, in particular, parylene. This adsorbent polymer layer 16 of parylene is approximately 230,000 Å thick. Bioactive material layer 18 of the antiplatelet GP IIb/IIIa antibody (AZ1) was passively loaded on adsorbent polymer layer 16. The polymer coated stainless steel stents were immersed for approximately 24 hours in a buffered aqueous solution of AZ1 antibody (1 mg/ml, pH=7.2) at 37° C. AZ1 is a monoclonal anti-rabbit platelet glycoprotein (GP) IIb/IIIa antibody. Using radio-labeled AZ1, it was demonstrated that approximately 0.02 µg antibody was loaded per mm² stent surface area (approximately 2 µg total for a 3×20 mm GR II™ stent). It was also demonstrated that in an in-vitro flow system (10 ml/min, 1% BSA in PBS) approximately half the loaded antibody remained on the stent after approximately 10 days perfusion.

The mechanism by which the stent is loaded with drug are thought to include adsorption onto the surface of the polymer layer and/or absorption into the polymer.

Previous studies with similar loading and release of AZ1 from cellulose coated stainless steel stents showed inhibition of platelet aggregation and reduced thrombosis rates in a rabbit model of deep arterial injury. (Aggarwal et al., *Antithrombotic Potential of Polymer-Coated Stents Eluting Platelet Glycoprotein IIb/IIIa Receptor Antibody*, American Heart Association Circulation Vol. 94 No. 12, Dec. 15, 1996, pp3311-3317).

In another example, c7E3 Fab as bioactive material layer 18 is attached to polymer coating layer 16. Bioactive material c7E3 Fab is a chimeric monoclonal antibody that acts upon the Gp IIa/IIIb integrin on platelets to inhibit their aggregation. This antibody or receptor blocker can be used in humans intravenously to prevent thrombosis during coronary angioplasty. This receptor blocker is also known as ReoPro™ available from Eli Lilly, Indianapolis, Ind. Bioactive material layer 18 of the antiplatelet GP IIb/IIIa antibody (c7E3 Fab) was passively loaded on adsorbent polymer layer 16. The polymer coated stainless steel stents were immersed for approximately 24 hours in a buffered aqueous solution of c7E3 Fab antibody (1 mg/ml, pH=7.2) at 37° C. c7E3 Fab is an inhibitor of platelet thrombus in humans. Using radio-labeled c7E3 Fab, it was demonstrated that approximately 0.010 µg antibody was loaded per mm² stent surface area (approximately 10 µg total for a 3×20 mm GR II™ stent). It was also demonstrated that in an in-vitro flow system (10 ml/min, 1% BSA in PBS) approximately half the loaded antibody remained on the stent after approximately 10 days perfusion.

Figure 12:
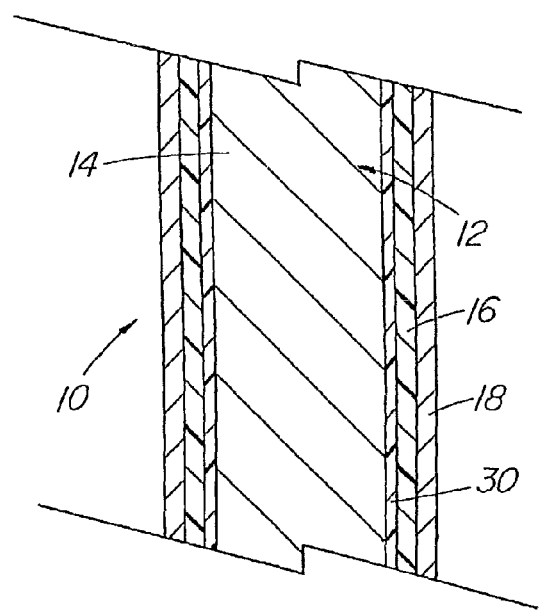
FIG. 12 depicts still another aspect of the medical device of FIG. 11 in which the polymer coating layer is adhered to the outer surface of the device base material using an adhesive promotion layer.

FIG. 12 depicts still another aspect of device 10 of FIG. 11. In this embodiment, a parylene adhesion promotion layer 30 is first applied to stainless steel base material 14 of structure 12. By way of example, adhesion promotion layer 30 is a thin layer of silane having a thickness in the range of, for example, 0.5 to 5,000 Å and preferably, 2 to 50 Å. This silane promotion layer is preferably A-174 silane including a gamma-methacryloxypropyltrimethoxysilane, which is available from Specialty Coating Systems Inc., Indianapolis, Ind. In preparing the outer surface of base material 14, it is first cleaned with isopropyl alcohol. The stent is then dipped in the silane to apply a very thin layer thereof to the outer surface of the base material. Polymer coating layer 16 of parylene is then applied to the silane layer. Other methods of preparing the outer surface of base material 14 include plasma etching and grit blasting. Preparation includes cleaning the outer surface of the base material with isopropyl alcohol, plasma etching the outer surface of the base material and applying the silane to the plasma etched surface. With grit blasting, the outer surface of the base material is grit blasted and then cleaned with isopropyl alcohol to which silane is applied to the cleansed grit blasted surface.

Figure 2:
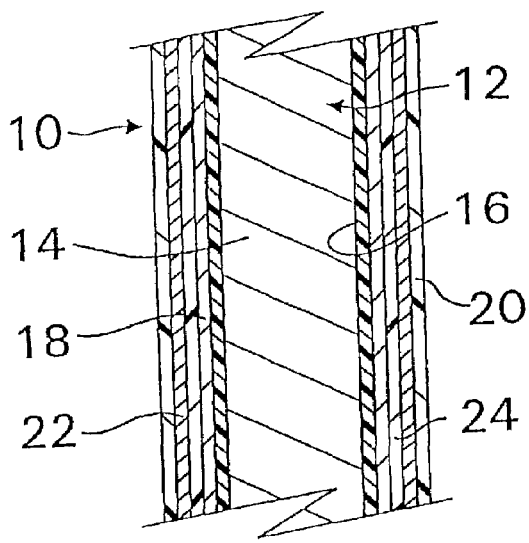
FIG. 2 is a cross-sectional view of another preferred embodiment of the present invention.

As shown in FIG. 2, the device 10 of the present invention is not limited to the inclusion of a single layer 18 of bioactive material. The device can, for example, comprise a second layer 22 of a bioactive material posited over the structure 12. The bioactive material of the second layer 22 can be, but need not necessarily be, different from the bioactive material of the first bioactive material layer 18, only that they not be posited on the same surface of the device 10 without the intermediate porous layer 24. The use of different materials in the layers 18 and 22 allows the device 10 to perform more than a single therapeutic function.

Figure 8:
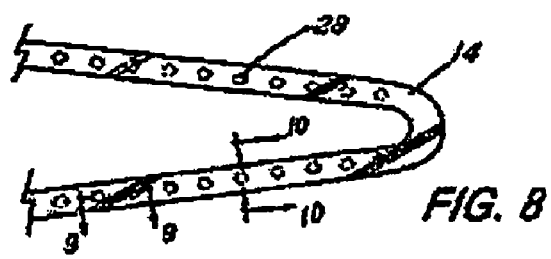
FIG. 8 is a partial, enlarged top view of FIG. 7.
Figure 9:
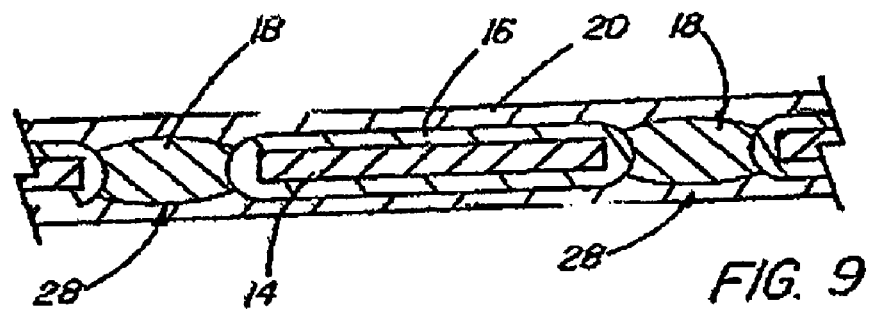
FIG. 9 is an enlarged, sectional view along lines 9-9 of FIG. 8.

The device 10 of the present invention can further comprise an additional porous layer 24 of the polymer posited between each of the layers 18 and 22 of bioactive material. It is reiterated that bioactive material 18 is on one surface of structure 12. The other surface may be free of bioactive material or may comprise one or more different bioactive materials. The additional porous layer 24 can give the bioactive materials in the layers 18 and 22 different release rates. Simultaneously, or alternatively, the device 10 may employ bioactive materials in the two layers 18 and 22 which are different from one another and have different solubilities. In such a case, it is advantageous and preferred to position the layer 22 containing the less soluble bioactive material above the layer 18 containing the more soluble bioactive material. Alternatively, the bioactive material 18 may be contained in holes, wells, slots and the like occurring within the stent surface as illustrated in FIGS. 8-10 and will further be discussed in greater detail.

For example, when the structure 12 of the device 10 is configured as a vascular stent, it is advantageous for the at least one layer 18 to contain relatively soluble heparin, and the second layer 22 to contain relatively less soluble dexamethasone. Unexpectedly, the heparin promotes the release of the dexamethasone, increasing its release rate many times over the release rate of dexamethasone in the absence of heparin. The release rate of the heparin is also lowered, some-what less dramatically than the increase of the dexamethasone release rate. More particularly, when dexamethasone is disposed by itself beneath a porous parylene layer 20 dimensioned as disclosed above, its release rate is negligible; an adequate release rate is obtained only when the thickness of the porous layer 20 is reduced by a factor of ten or more. In contrast, when a layer 22 of dexamethasone is disposed over a layer 18 of heparin, and beneath a porous parylene layer 20 dimensioned as above, the dexamethasone may be released at a desirable rate of about 1 to 10 $\mu g/cm^2$ per day. Moreover, and even more unexpectedly, this increased release rate for the dexamethasone is thought to be maintained even after all of the heparin has been released from the layer 18.

The bioactive material layers 18 and/or 22 are applied to the device 10 independent of the application of the porous polymer layers 20 and/or 24. Any mixing of a bioactive material from the layers 18 and/or 22 into the porous layers 20 and/or 24, prior to introducing the device 10 into the vascular system of the patient, is unintentional and merely incidental. This gives significantly more control over the release rate of the bioactive material than the simple dispersal of a bioactive material in a polymeric layer.

Figure 3:
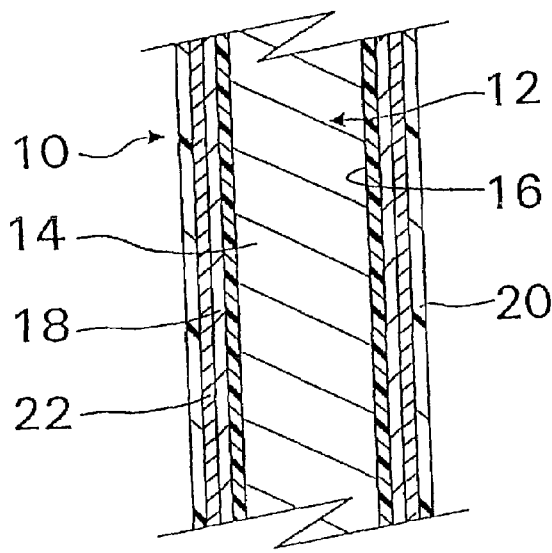
FIG. 3 is a cross-sectional view of yet another preferred embodiment of the present invention.

The device 10 need not include the additional porous layer 24 when two or more layers 18 and 22 of bioactive material are present. As shown in FIG. 3, the layers 18 and 22 do not have to be separated by a porous layer, but can instead lie directly against one another. It is still advantageous in this embodiment to position the layer 22 containing the relatively less soluble bioactive material above the layer 18 containing the relatively more soluble bioactive material.

Whether or not the additional porous layer 24 is present, it is preferred that the layers 18 and 22 contain about 0.05 to 2.0 mg of each of heparin and dexamethasone, respectively, per 1 $cm^2$ of the gross surface area of the structure 12. The total amount of bioactive material posited in the layers 18 and 22 over the structure 12 is thus preferably in the range of about 0.1 to 10 $mg/cm^2$.

Some dexamethasone derivatives, such as dexamethasone sodium phosphate, are substantially more soluble than dexamethasone itself. If a more soluble dexamethasone derivative is used as the bioactive material in the device 10 of the present invention, the thickness of the at least one porous layer 20 (and of the additional porous layer 24) should be adjusted accordingly.

The particular structure of the device 10 as disclosed may be adapted to specific uses in a variety of ways. For example, the device 10 may include further layers of the same or different bioactive materials. These additional layers of bioactive material may or may not be separated by additional porous layers, as convenient or desired. Alternatively, additional porous layers may separate only some of the additional layers of bioactive material. Moreover, one bioactive material may be placed on one portion of the structure 12 of the device 10, and another bioactive material placed on a different portion of the structure 12 of the device 10.

Figure 4:
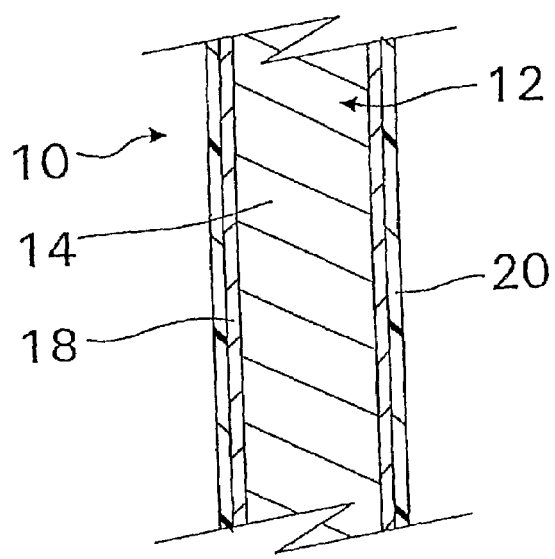
FIG. 4 is a cross-sectional view of a further preferred embodiment of the present invention.

Alternatively, the device 10 need not include the additional coating layer 16 at all. Such a configuration is shown in FIG. 4, in which the bioactive material layer 18 is posited directly atop the base material 14 of the structure 12. In such a case, it may be highly advantageous to surface process or surface activate the base material 14, to promote the deposition or adhesion of the bioactive material on the base material 14, especially before the depositing of the at least one porous layer 20. Surface processing and surface activation can also selectively alter the release rate of the bioactive material. Such processing can also be used to promote the deposition or adhesion of the additional coating layer 16, if present, on the base material 14. The additional coating layer 16 itself, or any second or additional porous layer 24 itself, can similarly be processed to promote the deposition or adhesion of the bioactive material layer 18, or to further control the release rate of the bioactive material.

Useful methods of surface processing can include any of a variety of such procedures, including: cleaning; physical modifications such as etching, drilling, cutting, or abrasion; and chemical modifications such as solvent treatment, the application of primer coatings, the application of surfactants, plasma treatment, ion bombardment and covalent bonding.

It has been found particularly advantageous to plasma treat the additional coating layer 16 (for example, of parylene) before depositing the bioactive material layer 18 atop it. The plasma treatment improves the adhesion of the bioactive material, increases the amount of bioactive material that can be deposited, and allows the bioactive material to be deposited in a more uniform layer. Indeed, it is very difficult to deposit a hygroscopic agent such as heparin on an unmodified parylene surface, which is hydrophobic and poorly wettable. However, plasma treatment renders the parylene surface wettable, allowing heparin to be easily deposited on it.

Any of the porous polymer layers 20 and 24 may also be surface processed by any of the methods mentioned above to alter the release rate of the bioactive material or materials, and/or otherwise improve the biocompatibility of the surface of the layers. For example, the application of an overcoat of polyethylene oxide, phosphatidylcholine or a covalently bound bioactive material, e.g., covalently attached heparin to the layers 20 and/or 24 could render the surface of the layers more blood compatible. Similarly, the plasma treatment or application of a hydrogel coating to the layers 20 and/or 24 could alter their surface energies, preferably providing surface energies in the range of 20 to 30 dyne/cm, thereby rendering their surfaces more biocompatible.

Figure 5:
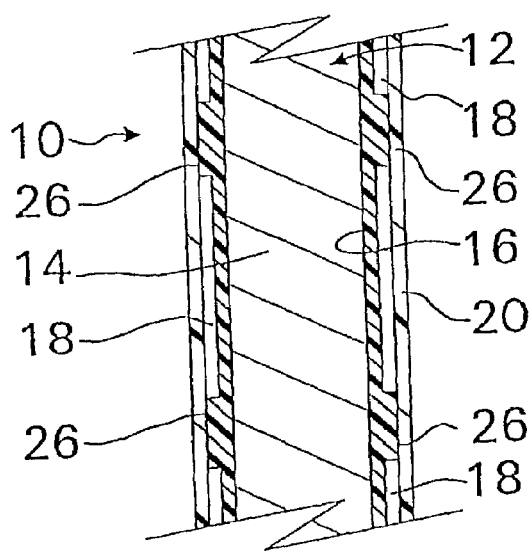
FIG. 5 is a cross-sectional view of an additional preferred embodiment of the present invention.

Referring now to FIG. 5, an embodiment of the device 10 is there shown in which a mechanical bond or connector 26 is provided between (a) any one of the porous layers 20 and 24, and (b) any or all of the other of the porous layers 20 and 24, the additional coating layer 16 and the base material 14. The connector 26 reliably secures the layers 16, 20 and/or 24 to each other, and or to the base material 14. The connector 26 lends structural integrity to the device 10, particularly after the bioactive material layer or layers 18 and/or 20 have been fully released into the patient.

For simplicity, the connector 26 is shown in FIG. 5 as a plurality of projections of the base material 14 securing a single porous layer 20 to the base material 14. The connector 26 may alternatively extend from the porous layer 20, through the bioactive material layer 18, and to the base material 14. In either case, a single layer 18 of bioactive material, divided into several segments by the connector 26, is posited between the porous layer 20 and the base material 14. The connectors can also function to partition the different bioactive agents into different regions of the device's surface.

The connector 26 may be provided in a variety of ways. For example, the connector 26 can be formed as a single piece with the base material 14 during its initial fabrication or molding into the structure 12. The connector 26 can instead be formed as a distinct element, such as a bridge, strut, pin or stud added to an existing structure 12. The connector 26 can also be formed as a built-up land, shoulder, plateau, pod or pan on the base material 14. Alternatively, a portion of the base material 14 between the desired locations of plural connectors 26 may be removed by etching, mechanical abrasion, or the like, and the bioactive material layer 18 deposited between them. The connector 26 can also be formed so as to extend downwards towards the base material 14, by wiping or etching away a portion of a previously applied bioactive material layer 18, and allowing the porous layer 20 to deposit by vapor deposition or plasma deposition directly on the bare portions of the base material 14. Other ways to expose a portion of the base material 14 to direct connection to the porous layer 20 will be evident to those skilled in this area.

Figure 7:
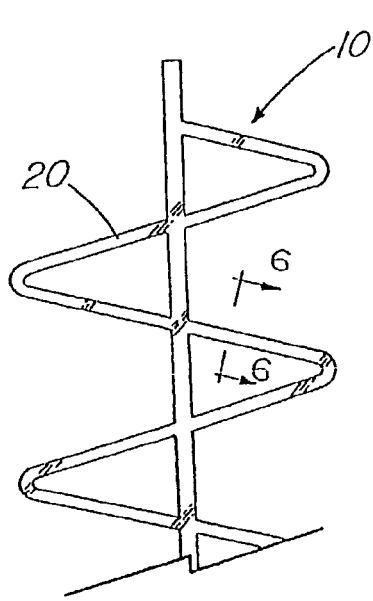
FIG. 7 is a cross-sectional view of an additional preferred embodiment of the present invention.
Figure 6A:
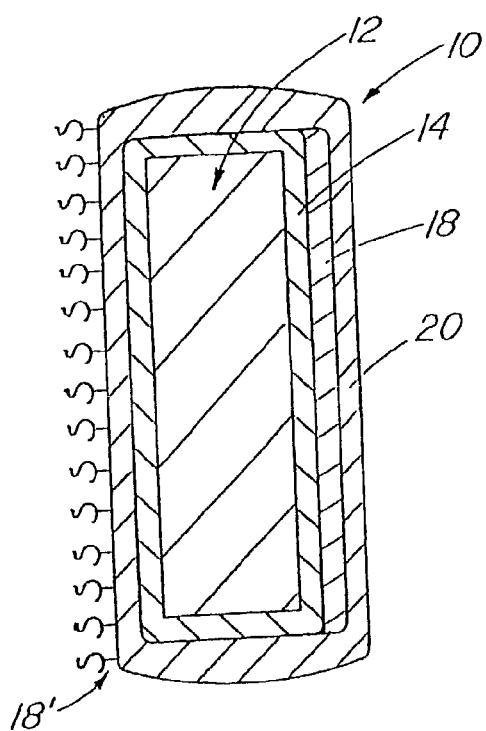
FIGS. 6A and 6B are cross-sectional views of an additional preferred embodiment of the present invention.
Figure 6B:
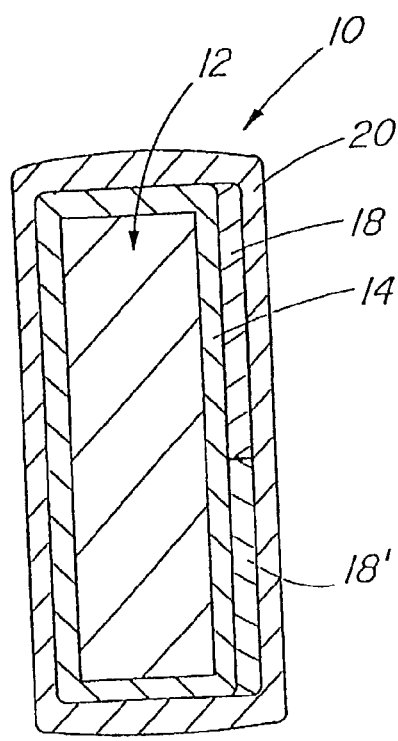

In another preferred embodiment, as illustrated in FIGS. 6A, 6B and 7, a bioactive material 18 is posited on the one surface of base material 14 making up structure 12 in FIG. 6A. FIG. 7 shows a stent 10 in its flat or planar state prior to being coiled and showing porous layer 20 applied to its outermost surface. FIGS. 6A and 6B are section views along line 6-6 of FIG. 7. The bioactive material 18 posited on the one surface of base material 14 in FIG. 6A may be a number of different therapeutic and/or diagnostic agents. For example, the device 10 may be a stent which is placed in the body of a patient near a tumor to deliver a chemotherapeutic agent, such as tamoxifen citrate or Taxol®, directly to the tumor. A porous layer 20 is posited over the bioactive material 18 to provide a smoother surface as well as a more controlled release of the bioactive material 18. As further illustrated in FIG. 6A, the opposite surface of the device may have, for example, heparin 18' covalently bonded to porous layer 20, particularly where this surface faces, for example, the lumen of a blood vessel, to provide antithrombotic effect and blood compatibility. It is pointed out, as has been discussed herein, a third but different bioactive material may be posited (not shown) on the opposite surface of base material 14 from the first bioactive material 18 and on the same side of base material 14 as the covalently bound heparin or any other bioactive material including other covalently bound bioactive materials and separated by porous layer 20.

A variation of the embodiment shown in FIG. 6A is illustrated in FIG. 6B, where two bioactive materials 18 and 18' are posited on the same surface of base material 14 of structure 12. A porous layer 20 may be deposited over the bioactive materials 18 and 18' as well as the bioactive-material-free surface of based material 14. This embodiment illustrates a situation where it may be desirable to deliver two agents to the tissue to which the particular surface of device 10 is exposed, e.g., an antiinflammatory agent and an antiviral agent. Moreover, the opposite surface of the device free of bioactive material is available for positing one or more bioactive materials or therapeutic agents, e.g., an antithrombotic agent.

As has been previously discussed, multiple layers of bioactive materials and porous layers may be applied to the device 10 where the limiting factors become the total thickness of the device, the adhesion of multiple layers and the like.

Figure 10A:
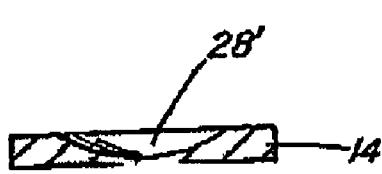
FIGS. 10A-10D are enlarged cross-sectional views along lines 10-10 of FIG. 8.
Figure 10C:
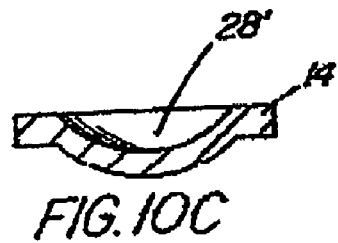
Figure 10B:
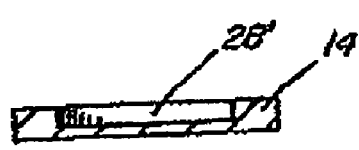
Figure 10D:

In still another embodiment of the present invention, the device of the present invention includes apertures within the device for containing the bioactive material. This embodiment is illustrated in FIGS. 8, 9, 10A, 10B, 10C and 10D. FIG. 8 shows an arm of the stent of FIG. 7 wherein the arm includes holes 28 into which a bioactive material is contained. FIG. 9 shows a section of the arm of the stent along lines 9-9 of FIG. 8. Bioactive material 18 is contained within the hole 28 where the base material 14 contains coating 16 and further where porous layer 20 forms the outer most layer for the bioactive material 18 to diffuse through. In an alternative embodiment, wells 28' may be cut, etched or stamped into the base material 14 of the device in which a bioactive material 18 may be contained. This embodiment is illustrated in FIGS. 10A, 10B, 10C and 10D which are partial cross-sectional FIGs. taken along line 10-10 of FIG. 8. Only the features of layer (14) are shown. The wells 28' may also be in the form of slots or grooves in the surface of the base material 14 of the medical device. This aspect of the invention provides the advantage of better controlling the total amount of the bioactive material 18 to be released as well as the rate at which it is released. For example, a V-shape well 28', as illustrated in FIG. 10D, will contain less quantity of bioactive material 18 and release the material at geometric rate as compared to a square shaped well 28', as illustrated in FIG. 10B, which will have a more uniform, linear release rate.

The holes, wells, slots, grooves and the like, described above, may be formed in the surface of the device 10 by a variety of techniques. For example, such techniques include drilling or cutting by utilizing lasers, electron-beam machining and the like or employing photoresist procedures and etching the desired apertures.

All the bioactive materials discussed above that may be coated on the surface of the device 10 may be used to be contained within the apertures of this aspect of the invention. Likewise, layers of bioactive materials and porous layers may be applied and built up on the exterior surfaces of the device as described previously with regard to other aspects of the invention, e.g., heparin, may be covalently bound to one surface of the device illustrated in FIG. 9.

The method of making the device 10 according to the present invention may now be understood. In its simplest form, the method comprises the steps of depositing the at least one layer 18 of bioactive material over the structure 12, followed by depositing the at least one porous layer 20, preferably by vapor deposition or plasma deposition, over the at least one bioactive material layer 18 on the one surface of structure 12. The at least one porous layer 20 being composed of a biocompatible polymer and being of a thickness adequate to provide a controlled release of the bioactive material. Preferably, the at least one additional coating layer 16 is first posited by vapor deposition directly on the base material 14 of the structure 12. Such deposition is carried out by preparing or obtaining di-p-xylylene or a derivative thereof, sublimating and cracking the di-p-xylylene or derivative to yield monomeric p-xylylene or a monomeric derivative, and allowing the monomer to simultaneously condense on and polymerize over the base material 14. The deposition step is carried out under vacuum, and the base material 14 maintained at or near room temperature during the deposition step. The deposition is carried out in the absence of any solvent or catalyst for the polymer, and in the absence of any other action to aid polymerization. One preferred derivative for carrying out the deposition step is dichloro-di-p-xylylene. The parylene or parylene derivative is preferably applied at the thickness disclosed above, to yield a coating layer 16 which is substantially nonporous, but in any event less porous than the at least one porous layer 20 to be applied. If required by the composition of the coating layer 16, the layer 16 is then surface processed in an appropriate manner, for example, by plasma treatment as disclosed above.

The at least one layer 18 of the desired bioactive material or materials is then applied to the one surface of the structure 12, and in particular, onto the additional coating layer 16. This application step can be carried out in any of a variety of convenient ways, such as by dipping, rolling, brushing or spraying a fluid mixture of the bioactive material onto the additional coating layer 16, or by electrostatic deposition of either a fluid mixture or dry powder of the bioactive material, or by any other appropriate method. Different bioactive agents may be applied to different sections or surfaces of the device.

It can be particularly convenient to apply a mixture of the bioactive material or materials and a volatile fluid over the structure, and then remove the fluid in any suitable way, for example, by allowing it to evaporate. When heparin and/or dexamethasone or its derivatives serve as the bioactive material(s), the fluid is preferably ethyl alcohol. The bioactive material is preferably applied in an amount as disclosed above.

Other methods of depositing the bioactive material layer 18 over the structure 12 would be equally useful. Without regard to the method of application, however, what is important is that the bioactive material need only be physically held in place until the porous layer 20 is deposited over it. This can avoid the use of carriers, surfactants, chemical binding and other such methods often employed to hold a bioactive agent on other devices. The additives used in such methods may be toxic, or the additives or methods may alter or degrade the bioactive agent, rendering it less effective, or even toxic itself. Nonetheless, if desired these other methods may also be employed to deposit the bioactive material layer 18 of the present invention.

The bioactive material may, of course, be deposited on the one surface of the structure 12 as a smooth film or as a layer of particles. Moreover, multiple but different bioactive materials may be deposited in a manner that different surfaces of the device contain the different bioactive agents. In the latter case, the particle size may affect the properties or characteristics of the device 10, such as the smoothness of the uppermost porous coating 20, the profile of the device 10, the surface area over which the bioactive material layer 18 is disposed, the release rate of the bioactive material, the formation of bumps or irregularities in the bioactive material layer 18, the uniformity and strength of adhesion of the bioactive material layer 18, and other properties or characteristics. For example, it has been useful to employ micronized bioactive materials, that is, materials which have been processed to a small particle size, typically less than 10 µm in diameter. However, the bioactive material may also be deposited as micro-encapsulated particles, dispersed in liposomes, adsorbed onto or absorbed into small carrier particles, or the like.

In still another embodiment according to the present invention, the bioactive material may be posited on the one surface of structure 12 in a specific geometric pattern. For example, the tips or arms of a stent may be free of bioactive material, or the bioactive material may be applied in parallel lines, particularly where two or more bioactive materials are applied to the same surface.

In any event, once the bioactive material layer 18 is in place, the at least one porous layer 20 is then applied over the at least one bioactive material layer 18 in the same manner as for the application of the at least one additional coating 16. A polymer such as parylene or a parylene derivative is applied at the lesser thickness disclosed above, however, so as to yield the at least one porous layer 20.

Any other layers, such as the second bioactive material layer 22 or the additional porous layer 24, are applied in the appropriate order and in the same manner as disclosed above. The steps of the method are preferably carried out with any of the bioactive materials, structures, and base materials disclosed above.

Of course, polyimide may be deposited as any or all of the porous and additional coating layers 20, 24 and/or 16 by vapor deposition in a manner similar to that disclosed above for parylene and its derivatives. Techniques for the plasma deposition of polymers such as poly(ethylene oxide), poly(ethylene glycol), poly(propylene oxide), silicone, or a polymer of methane, tetrafluoroethylene or tetramethyl-disiloxane on other objects are well-known, and these techniques may be useful in the practice of the present invention.

Another technique for controlling the release of the bioactive material may include depositing monodispersed polymeric particles, i.e., referred to as porogens, on the surface of the device 10 comprising one or more bioactive materials prior to deposition of porous layer 20. After the porous layer 20 is deposited and cured, the porogens may be dissolved away with the appropriate solvent, leaving a cavity or pore in the outer coating to facilitate the passage of the underlying bioactive materials.

The method of using the device 10 of the present invention in medically treating a human or veterinary patient can now be easily understood as well. The method of the present invention is an improvement over previous methods which include the step of inserting into a patient an implantable vascular device 10, the device 10 comprising a structure 12 adapted for introduction into the vascular system of a patient, and the structure 12 being composed of a base material 14. The method according to the present invention comprises the preliminary steps of depositing at least one layer 18 of a bioactive material on one surface of the structure 12, followed by depositing at least one porous layer 20 over the at least one bioactive material layer 18, the porous layer 20 being composed of a polymer and having a thickness adequate to provide a controlled release of the bioactive material when the device 10 is positioned in the patient's vascular system.

The method can further entail carrying out the two depositing steps with the various embodiments of the device 10 disclosed above, in accordance with the method of making the device 10 disclosed above. More particularly, the step of depositing the at least one porous layer 20 can comprise polymerizing the at least one layer 20 from a monomer vapor, preferably a vapor of parylene or a parylene derivative, free of any solvent or catalyst. The method can also comprise the step of depositing the at least one additional coating layer 16 between the structure 12 and the at least one bioactive material layer 18.

The method of treatment according to the present invention is completed by inserting the device 10 into the vascular system of the patient. The at least one porous layer 20 and any additional porous layers 24 automatically release the bioactive material or materials in a controlled fashion into the patient.

The remaining details of the method of medical treatment are the same as those disclosed with respect to the method of making the device 10 of the present invention; for the sake of brevity, they need not be repeated here.

In view of the disclosure above, it is clear that the present invention provides an implantable medical device which achieves precise control over the release of one or more bioactive materials contained in the device. Moreover, the polyimide, parylene, parylene derivative or other polymeric layers 16, 20 and/or 24 can be remarkably thin, in comparison to the thicknesses required for other polymer layers. The bulk or substantial majority of the overall coating on the structure 12 can therefore consist of bioactive material. This allows the supply of relatively large quantities of bioactive material to the patient, much greater than the amounts supplied by prior devices. These quantities of bioactive material can be supplied to any of a wide variety of locations within a patient during or after the performance of a medical procedure, but are especially useful for preventing abrupt closure and/or restenosis of a blood vessel by the delivery of an antithrombic or other medication to the region of it which has been opened by PTA. The invention permits the release rate of a bioactive material to be carefully controlled over both the short and long terms. Most importantly, any degradation of the bioactive material which might otherwise occur by other polymer coating techniques is avoided.

As noted above, the structure 12 of the medical device 10 of the present invention is most preferably configured as a vascular or other stent. The typical dimensions given above for a vascular stent are about 10 to 60 mm in length and an expanded diameter of about 2 to 6 mm when inserted into the vascular system of a patient. It is believed that these and other specific disclosures made herein, along with an inspection of the drawing, attention to the disclosure of the specific commercial examples of suitable stents noted above and the general knowledge of stents possessed by anyone having even rudimentary skills in this art, make it abundantly clear that such a vascular stent is cylindrical in shape. Indeed, a tubular or cylindrical, thin-walled shape is characteristic of vascular and other stents; see, for example, U.S. Pat. No. 4,580,568 (Gianturco, Apr. 8, 1986); U.S. Pat. No. 4,776,337 (Palmaz, Oct. 11, 1988); U.S. Pat. No. 4,907,336 (Gianturco, Mar. 13, 1990); U.S. Pat. No. 4,733,665 (Palmaz, Mar. 29, 1988); U.S. Pat. No. 4,739,762 (Palmaz, Apr. 26, 1988); U.S. Pat. No. 4,800,882 (Gianturco, Jan. 31, 1989); U.S. Pat. No. 5,102,417 (Palmaz, Apr. 7, 1992); U.S. Pat. No. 5,282,824 (Gianturco, Feb. 1, 1994); and U.S. Pat. No. 5,632,771 (Boatman et al., May 27, 1997), the entire disclosures of all of these being expressly incorporated by reference herein.

These patents disclose or describe just a few of the ways in which stents useful as the structure 12 in the present invention can be constructed. Useful stents can be self-expanding after introduction into a patient, can be expandable within a patient by an inflatable balloon or other mechanism, or can be fully expanded prior to introduction into a patient (the last either by expansion prior to introduction, or by being initially constructed at the desired diameter).

Useful stents can be of a stranded or filamentous type, comprising one or a plurality of strands or filaments of round, flat or other desirable cross-sectional shape, composed of a suitable base material. Each strand or filament can be individually or collectively bent, coiled, folded, woven, interlaced, wrapped, overlapped or otherwise formed into a generally cylindrical shape. That resulting shape can also be considered as a framework or scaffold composed of struts or elongate members, the struts or elongate members being portions of one or more strands or filaments. Such a shape can be formed, for example, as a wire mesh tube.

Useful stents can also be formed from a rolled sheet of a suitable base material and having one or more ports, openings, holes, perforations, slots, recesses, grooves or the like formed therein, for example, by laser cutting. Useful stents can further be formed from a tube or cannula of a suitable base material and having one or more ports, openings, holes, perforations, slots, recesses, grooves or the like formed therein, for example, by laser cutting.

The base material of the shape, framework or scaffold of these or other types of stents can be any of the materials listed above. Any of these or other types of stents can be partly or fully covered by a flexible and preferably imperforate sleeve or coating so as to prevent the intrusion of tissue or other matter into or through any spaces in the shape, framework or scaffold it covers. The nature of the sleeve or coating will determine whether it is more sensible to consider the sleeve or coating to be part of the structure 12 or the at least one coating layer 16 on the structure 12. Without regard to how the sleeve or coating is considered, however, its use will plainly fall within the scope of the present invention.

The identification of these types of stents, and the identification above of certain patents disclosing examples of useful stents, should not be taken as a suggestion that the present invention is useful only with these types or examples of stents. To the contrary; the present invention is expected to be able to successfully employ stents of many different kinds.

With particular regard to the embodiments of FIGS. 7 through 10D herein, it has already been noted that FIG. 7 discloses a stent having a plurality of arms shown in a flat or planar state prior to being coiled. Again, in view of the common knowledge in the art, it would appear to be abundantly clear to anyone having even rudimentary skills in this art that such coiling could only yield a stent having a thin-walled, cylindrical shape. It was further noted above that the walls 28' may be laser cut, etched or stamped into the base material 14 of the arm of the stent, and that the wells 28' can be square shaped (FIG. 10B), or can be slots or grooves.

Accordingly, it should be clear that the foregoing disclosure and accompanying drawing necessarily and inherently disclose further characterizing features of a stent within the scope of the present invention, such necessarily disclosed features permitting the stent to be described in terms of its thin-walled, cylindrical shape.

Thus, in an additional aspect, the present invention can be characterized as being directed to a stent comprising a generally thin walled cylinder, the cylinder having or containing a plurality of arms, the arms being expandable and having a generally uniform thickness; and at least one well 28' formed in at least one of the arms, the well 28' having a closed perimeter on all sides and an open top, and the well 28' being smaller in all dimensions than the arm, the well 28' containing a therapeutic agent applied therein and wherein the therapeutic agent is an immunosuppressive agent. The wall 28' can be generally rectangular or square in shape. The immunosuppressive agent is preferably cyclosporin.

In a further aspect, the present invention can be characterized as being directed to a stent comprising a generally thin walled cylinder, the cylinder having or containing a plurality of arms, the arms being expandable dependent on the amount of force applied to the arms, and the arms having a generally uniform thickness; and at least one well 28' formed in at least one of the arms, the well 28' having a closed perimeter on all sides and an open top, and the well 28' being smaller in all dimensions than the arm, the well 28' containing a therapeutic agent applied therein; wherein the well 28' has a generally rectangular perimeter.

In yet another aspect, the present invention can be characterized as being directed, in combination, to a stent comprising a generally thin walled cylinder, the cylinder having or containing a plurality of arms, the arms being expandable dependent on the amount of force applied to the arms, and the arms having a generally uniform thickness; and at least one well 28' formed in at least one of the arms, the well 28' having a closed perimeter on all sides and an open top, and the well 28' being smaller in all dimensions than the arm, the well 28' containing a therapeutic agent applied therein; wherein the well 28' has a generally rectangular perimeter; and wherein the therapeutic agent is an immunosuppressive agent coated on the well 28'. The well 28' can be laser cut into the arm. As before, the immunosuppressive agent is preferably cyclosporin.

In a still further aspect, the present invention can be characterized as being directed to a stent comprising a generally thin walled structure having or containing a plurality of arms, the arms expandable to assume the shape of a lumen into which the stent is emplaced, the arms having a thickness, and at least one well 28' formed in at least one of the arms, the well 28' having a closed perimeter on all sides and an open top, and the well 28' being smaller in all dimensions than the arm, the well 28' containing a therapeutic agent applied therein and wherein the therapeutic agent is an immunosuppressive agent. Again, the immunosuppressive agent is preferably cyclosporin.

In another aspect, the present invention can be characterized as being directed to a stent comprising a generally thin walled cylinder, the cylinder having or containing a plurality of generally solid arms, the arms being expandable dependent on the amount of force applied to the arms, and at least one well 28' formed in at least one of the arms, the well 28' having a closed perimeter on all sides and an open top, and the well 28' being smaller in all dimensions than the arm, the well 28' containing a reservoir of a therapeutic agent applied therein.

In an additional aspect, the present invention can be characterized as being directed to an expandable, self-expanding or expanded stent including a base material, wherein at least one well 28' is formed in the base material of the stent, the at least one well 28' containing a bioactive material applied therein. The bioactive material can be an immunosuppressive agent, an anti-proliferative, an antibiotic, and anti-inflammatory, a growth factor inhibitor or a remodeling inhibitor. The immunosuppressive agent is preferably cyclosporin. The well 28' can be configured as a groove.

The details of these aspects of the invention have already been described with respect to other embodiments of the present invention, and therefore need not (and for brevity, will not) be repeated.

The other details of the construction or composition of the various elements of the disclosed embodiment of the present invention are not believed to be critical to the achievement of the advantages of the present invention, so long as the elements possess the strength or flexibility needed for them to perform as disclosed. The selection of these and other details of construction are believed to be well within the ability of one of ordinary skills in this area, in view of the present disclosure.

INDUSTRIAL APPLICABILITY

The present invention is useful in the performance of vascular surgical procedures, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts. It is contemplated that only part of a device need be coated. Furthermore, different parts of the device can be coated with different bioactive materials or coating layers. It is also contemplated that different sides or regions of the same part of a device can be coated with different bioactive materials or coating layers.

What is claimed is:

1. An implantable medical device, comprising:
an expandable stent sized and shaped for introduction into a vascular system of a patient, the expandable stent having at least one surface;
a coating layer in direct contact with the at least one surface and comprising a first polymer posited between the at least one surface of the expandable stent and at least one layer comprising a bioactive agent;
the porous layer comprising a second polymer posited over the at least one layer comprising a bioactive agent and controlling the release of the bioactive agent, the first polymer and the second polymer being the same or different;
wherein the expandable stent is capable of eluting the bioactive agent from the bioactive layer through the porous layer when the expandable stent is placed in the vascular system of the patient;
wherein said stent is a metal stent, and said at least one surface is a metal surface;
wherein said coating layer is in contact with said metal surface; and
wherein said first polymer is a parylene or a parylene derivative polymer.

2. An implantable medical device, comprising:
an expandable stent sized and shaped for introduction into a vascular system of a patient, the expandable stent having at least one surface;
a coating layer in direct contact with the at least one surface and comprising a first polymer posited between the at least one surface of the expandable stent and at least one layer comprising a bioactive agent;
the at least one layer comprising a bioactive agent posited over the coating layer and under a porous layer consisting essentially of one or more biocompatible polymers selected from the group consisting of: a parylene polymer, a poly(alkylmethacrylate) polymer, and an ethylene-vinyl acetate copolymer;
the porous layer posited over the bioactive agent and controlling the release of the bioactive agent;
wherein the expandable stent is capable of eluting the bioactive agent from the at least one layer comprising a bioactive agent through the porous layer when the expandable stent is placed in the vascular system of the patient; and
wherein the porous layer comprises a material selected from the group consisting of: parylene and poly(n-butyl methacrylate).

3. An implantable medical device, comprising:
an expandable stent sized and shaped for introduction into a vascular system of a patient, the expandable stent having at least one surface;
a coating layer in direct contact with the at least one surface and comprising a first polymer posited between the at least one surface of the expandable stent and at least one layer comprising a bioactive agent;
the at least one layer comprising a bioactive agent posited over the coating layer and under a porous layer consisting essentially of one or more biocompatible polymers selected from the group consisting of: a parylene polymer, a poly(alkylmethacrylate) polymer, and an ethylene-vinyl acetate copolymer;
the porous layer posited over the bioactive agent and controlling the release of the bioactive agent;
wherein the expandable stent is capable of eluting the bioactive agent from the at least one layer comprising a bioactive agent through the porous layer when the expandable stent is placed in the vascular system of the patient; and
wherein the bioactive agent consists essentially of an immunosuppressive agent and the porous layer consists essentially of a biocompatible polymer selected from the group consisting of: a parylene polymer, a poly(alkylmethacrylate) polymer and an ethylene-vinyl acetate copolymer.

4. The medical device of claim 1, wherein the metal surface comprises stainless steel.

5. The medical device of claim 1, wherein the expandable stent surface forms at least a portion of at least one hole, well, groove or slot in which the bioactive agent is contained.

6. The medical device of claim 1, wherein the porous layer comprises a biocompatible polymer selected from the group consisting of: parylene, poly(n-butyl-acrylate), poly(n-butyl methacrylate), poly 2-ethyihexyl acrylate, poly lauryl-acrylate, poly 2-hydroxy-propyl acrylate, polyvinyl chloride, polyvinyl methyl ether, polyvinylidene fluoride, polyvinylidene chloride, polyacrylonitrile, polystyrene, polyvinyl acetate, ethylenemethyl methacrylate copolymers, acrylonitrile-styrene copolymers, ethylene glycol diacrylate, ethylene glycol dimethacrylate, trimethylopropane triacrylate, trimethylopropane trimethacrylate, pentaerythritol tetraacrylate, pentaerythritol tetramethacrylate, 1,6-hexanediol dimethacrylate, diethyleneglycol dimethacrylate, N-methylol methacrylamide butyl ether, N-vinyl pyrrolidone, vinyl oleate, polyvinyl chloride, polyvinylidene fluoride, acrylonitrile butadiene styrene resins, polyamides, rayon, rayon-triacetate, cellulose, cellulose acetate, cellulose butyrate, cellulose acetate butyrate, cellophane, cellulose nitrate, cellulose propionate, carboxymethyl cellulose, poly(L-lactic acid), polycaprolactone, poly(lactide-co-caprolactone), poly(lactide-co-glycolide), poly(hydroxybutyrate), poly(hydroxybutyrate-co-valerate), poly(glycolic acid), poly(D,L-lactic acid), poly(glycolic acid-co-trimethylene carbonate), poly(trimethylene carbonate), poly(ethylene oxide), poly(D-lactic acid), fibrin, fibrinogen, cellulose, starch, collagen, phosphatidylcholine, hyaluronic acid, and polymers, copolymers and mixtures thereof.

7. The medical device of claim 2, wherein the expandable stent surface comprises at least one of a material selected from the group consisting of: stainless steel, tantalum, titanium, nitinol, gold, platinum, inconel, iridium, silver, tungsten, any biocompatible metal, any alloy of the aforementioned metals, carbon, carbon fiber, cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, any biocompatible polymeric material, polylactic acid, polyglycolic acid, a polyanhydride, polycaprolactone, polyhydroxybutyrate valerate, any biodegradable polymer, a protein, an extracellular matrix component, collagen, and fibrin.

8. The medical device of claim 2, wherein the expandable stent surface forms a portion of at least one well that is a groove or slot in which the bioactive agent is contained.

9. The medical device of claim 2, where the coating layer comprises a material selected from the group consisting of: parylene, poly(n-butyl-acrylate), poly(n-butyl methacrylate), poly 2-ethylhexyl acrylate, poly lauryl-acrylate, poly 2-hydroxy-propyl acrylate, polyvinyl chloride, polyvinyl methyl ether, polyvinylidene fluoride, polyvinylidene chloride, polyacrylonitrile, polystyrene, polyvinyl acetate, ethylenemethyl methacrylate copolymers, acrylonitrile-styrene copolymers, ethylene glycol diacrylate, ethylene glycol dimethacrylate, trimethylopropane triacrylate, trimethylopropane trimethacrylate, pentaerythritol tetraacrylate, pentaerythritol tetramethacrylate, 1,6-hexanediol dimethacrylate, diethyleneglycol dimethacrylate, N-methylol methacrylamide butyl ether, N-vinyl pyrrolidone, vinyl oleate, polyvinyl chloride, polyvinylidene fluoride, acrylonitrile butadiene styrene resins, polyamides, rayon, rayon-triacetate, cellulose, cellulose acetate, cellulose butyrate, cellulose acetate butyrate, cellophane, cellulose nitrate, cellulose propionate, carboxymethyl cellulose, poly(L-lactic acid), polycaprolactone, poly(lactide-co-caprolactone), poly(lactide-co-glycolide), poly(hydroxybutyrate), poly(hydroxybutyrate-co-valerate), poly(glycolic acid), poly(D,L-lactic acid), poly(glycolic acid-co-trimethylene carbonate), poly(trimethylene carbonate), poly(ethylene oxide), poly(D-lactic acid), fibrin, fibrinogen, cellulose, starch, collagen, phosphatidylcholine, hyaluronic acid, and polymers, copolymers and mixtures thereof.

10. The medical device of claim 2, wherein the bioactive agent consists essentially of an immunosuppressive agent.

11. The implantable medical device of claim 2, wherein: said stent is a metal stent, and said at least one surface is a metal surface; said coating layer is in contact with said metal surface; and said coating layer consists of a parylene or a parylene derivative polymer.

12. The implantable medical device of claim 2, wherein: said coating layer consists of a parylene or a parylene derivative polymer.

* * * * *